United States Patent
Schlechtingen et al.

(10) Patent No.: US 10,829,506 B2
(45) Date of Patent: Nov. 10, 2020

(54) AMINO- OR AMMONIUM-CONTAINING SULFONIC ACID, PHOSPHONIC ACID AND CARBOXYLIC ACID DERIVATIVES AND THEIR MEDICAL USE

(71) Applicant: GRI Bio, Inc., La Jolla, CA (US)

(72) Inventors: Georg Schlechtingen, Dresden (DE); Hans-Joachim Knölker, Dresden (DE); Tim Friedrichson, Dresden (DE); Gary Jennings, Dresden (DE); Tobias Braxmeier, Kuppenheim (DE)

(73) Assignee: GRI Bio, Inc., La Jolla, CA (US)

( * ) Notice: Subject to any disclaimer, the term of this patent is extended or adjusted under 35 U.S.C. 154(b) by 0 days.

(21) Appl. No.: 15/851,676

(22) Filed: Dec. 21, 2017

(65) Prior Publication Data

US 2018/0244703 A1 Aug. 30, 2018

Related U.S. Application Data

(62) Division of application No. 14/403,167, filed as application No. PCT/EP2012/059812 on May 25, 2012, now Pat. No. 9,850,265.

(30) Foreign Application Priority Data

May 26, 2011 (EP) .................... 11167752

(51) Int. Cl.

| | | |
|---|---|---|
| *C07F 9/40* | (2006.01) | |
| *A61K 31/205* | (2006.01) | |
| *A61K 31/4425* | (2006.01) | |
| *A61K 31/662* | (2006.01) | |
| *C07C 309/14* | (2006.01) | |
| *C07F 9/38* | (2006.01) | |
| *C07C 229/12* | (2006.01) | |
| *C07D 295/037* | (2006.01) | |
| *C07D 211/06* | (2006.01) | |
| *C07D 211/60* | (2006.01) | |
| *C07D 211/46* | (2006.01) | |
| *C07D 211/62* | (2006.01) | |

(52) U.S. Cl.
CPC .......... *C07F 9/4006* (2013.01); *A61K 31/205* (2013.01); *A61K 31/4425* (2013.01); *A61K 31/662* (2013.01); *C07C 229/12* (2013.01); *C07C 309/14* (2013.01); *C07D 211/06* (2013.01); *C07D 211/46* (2013.01); *C07D 211/60* (2013.01); *C07D 211/62* (2013.01); *C07D 295/037* (2013.01); *C07F 9/3808* (2013.01)

(58) Field of Classification Search
CPC ................................................. C07F 9/4006
See application file for complete search history.

(56) References Cited

U.S. PATENT DOCUMENTS

| | | |
|---|---|---|
| 3,280,179 A | 10/1966 | Ernst |
| 3,432,408 A | 3/1969 | Brown et al. |
| 3,623,990 A | 11/1971 | Cambre |
| 4,085,134 A | 4/1978 | Redmore et al. |
| 4,259,249 A | 3/1981 | Degenhardt |
| 5,545,667 A | 8/1996 | Wiersema et al. |
| 6,004,771 A | 12/1999 | Thornton |
| 6,136,857 A | 10/2000 | Wiersema et al. |
| 6,406,880 B1 | 6/2002 | Thornton |
| 9,573,886 B2 | 2/2017 | Schlechtingen et al. |
| 9,751,834 B2 | 9/2017 | Schlechtingen et al. |
| 9,850,265 B2 | 12/2017 | Schlechtingen et al. |
| 10,143,668 B2 | 12/2018 | Schlechtingen et al. |
| 2003/0185816 A1 | 10/2003 | Olesen |
| 2015/0232418 A1 | 8/2015 | Schlechtingen et al. |
| 2015/0284320 A1 | 10/2015 | Schlechtingen et al. |
| 2016/0016981 A1 | 1/2016 | Schlechtingen et al. |
| 2017/0157070 A1 | 6/2017 | Schlechtingen et al. |

(Continued)

FOREIGN PATENT DOCUMENTS

| | | |
|---|---|---|
| CA | 2886676 A1 | 11/2012 |
| CA | 2886683 A1 | 11/2012 |

(Continued)

OTHER PUBLICATIONS

Limanov et al., Khimiko-Farmatsevticheskii Zhurnal (1990), 24(1), pp. 36-38 (CAS SciFinder abstract).*

Limanov et al., Khimiko-Farmatsevticheskii Zhurnal (1990), 24(1), pp. 36-38.*

Kimanov et al., Khimiko-Farmatsevticheskii Zhurnal (1971), 5(1), pp. 9-13 (CAS SciFinder English language abstract).*

Kimanov et al., Khimiko-Farmatsevticheskii Zhurnal (1971), 5(1), pp. 9-13.*

Enjalbert et al., Journal of Fluorine Chemistry (1999), 93(2), pp. 145-152.*

(Continued)

*Primary Examiner* — Brian J Davis
(74) *Attorney, Agent, or Firm* — Mintz Levin Cohn Ferris Glovsky and Popeo P.C.

(57) ABSTRACT

The present invention relates to amino- or ammonium-containing sulfonic acid, phosphonic acid and carboxylic acid derivatives, in particular the compounds of formula 1, 2, 3, 4, 5 or 6 and their medical use, including their use in treatment, prevention or amelioration of an inflammatory, autoimmune and/or allergic disorder.

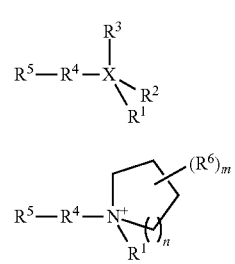

9 Claims, 10 Drawing Sheets

(56) References Cited

U.S. PATENT DOCUMENTS

Figure 1A:
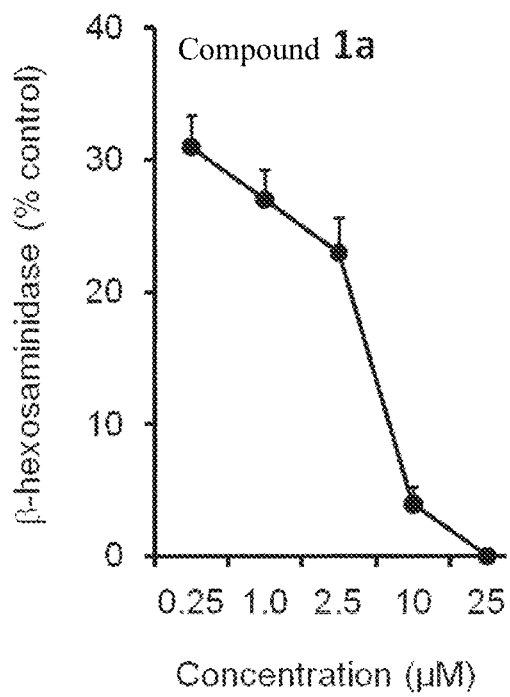

| | | |
|---|---|---|
| 2017/0369430 A1 | 12/2017 | Schlechtingen et al. |
| 2019/0175529 A1 | 6/2019 | Schlechtingen |

FOREIGN PATENT DOCUMENTS

| | | |
|---|---|---|
| CA | 2887385 C | 1/2017 |
| CN | 101 456 810 A | 6/2009 |
| EP | 0 569 028 A2 | 11/1993 |
| EP | 2 739 606 A1 | 6/2014 |
| EP | 2 809 318 A1 | 12/2014 |
| EP | 2 809 648 A1 | 12/2014 |
| FR | 1326561 A | 5/1963 |
| GB | 1 471 144 A | 4/1977 |
| GB | 1 541 427 A | 2/1979 |
| HK | 1204554 A | 11/2015 |
| HK | 1204602 A | 11/2015 |
| HK | 1198160 B | 7/2017 |
| JP | 2010-120998 A | 6/2010 |
| WO | WO 01/97837 A1 | 12/2001 |
| WO | WO 2005/000288 A2 | 1/2005 |
| WO | WO 2007/071402 A1 | 6/2007 |
| WO | WO 2009/136396 A2 | 11/2009 |
| WO | WO 2010/055028 A2 | 5/2010 |
| WO | WO 2012/160186 A1 | 11/2012 |
| WO | WO 2012/160187 A1 | 11/2012 |
| WO | WO 2012/160188 A1 | 11/2012 |

OTHER PUBLICATIONS

Birnie et al., "Antimicrobial Evaluation of N-Alkyl Betaines and N-Alkyl-N, N-Dimethylamine Oxides with Variations in Chain Length" Antimicrobial Agents and Chemotherapy, Sep. 2000, p. 2514-2517. vol. 44. No. 9.

Chen et al., "Inhibition of Geranylgeranyl Diphosphate Synthase by Bisphosphonates: A Crystallographic and Computational Investigation" Journal of Medical Chemistry, 2008, p. 5594-5607. vol. 51. No. 18.

Database Registry. Chemical Abstracts Service. RN 23035-15-6. Nov. 16, 1984.

Database Registry. Chemical Abstracts Service. RN 761356-67-6. Oct. 12, 2004.

Database CAPLUS in STN, Acc. No. 1967:30267, ERNST, U.S. Pat. No. 3,280,179 A (Oct. 18, 1966) (abstract).

Database CAPLUS in STN, Acc. No. 2001:935430, Olesen et al., US 2003/0185816 Al (part of patent family WO 2001/097837) (Oct. 2, 2003) (abstract).

Germanaud et al., "Summaries of neutral amphiphiles phosphobetaines to intercharge varying distances" Bulletin de la Sociètè Chimique de France, Jan.-Feb. 1988, p. 699-704.

Parris et al., "Soap Based Detergent Formulations. V. Amphoteric Lime Soap Dispersing Agents" Journal of the American Oil Chemists' Society, Dec. 1973, p. 509-511, vol. 50.

Rachinkskii et al., "N-Alkyl-N-Alkarboxymethylhexamethylenimmonium Derivatives" (Communication II of a series of works on the synthesis and investigation of hexamethylenimmonium compounds as bactericides) Zhurnal Prikladnoi Khimii, Oct. 1968, p. 2326-2329. vol. 41. No. 10.

Yan et al.,I "Design and synthesis of conformationally constrained 3-(N-alkylamino)propylphosphonic acids as potent agonists of sphingosine-1-phosphate (S1P) receptors" Bioorganic & Medicinal Chemistry Letters, Aug. 20, 2004, p. 4861-4866. vol. 14.

Banker, G. et al., "Prodrugs", Modern Pharmaceutics, Third Edition, Revised and Expanded, pp. 451 and 596, 1996,.

Bradding, P. et al., "The controversial role of mast cells in fibrosis", Immunological Reviews, vol. 282, pp. 198-231, 2018.

Bundgaard, H., "Chapter 1—Design of Prodrugs: Bioreversible derivatives for various functional groups and chemical entities", Design of Prodrugs, pp. 1-92, 1985.

Hargrove, L. et al., "Bile Duct Ligation-Induced Biliary Hyperplasia, Hepatic Injury, and Fibrosis Are Reduced in Mast Cell-Deficient KitW-sh Mice", Hepatology, vol. 65, No. 6, pp. 1991-2004, 2017.

Jarido, V. et al., "The emerging role of mast cells in liver disease", American Journal of Physiology-Gastrointestinal and Liver Physiology, vol. 313, pp. G89-G101, 2017.

Kennedy, L. et al., "Blocking H1/H2 histamine receptors inhibits damage/fibrosis in Mdr2−/− mice and human cholangiocarcinoma tumorigenesis", Hepatology, pp. 1-56, doi: 10.1002/hep.29898, Mar. 30, 2018, PMID:29601088 [Epub ahead of print].

Silverman, R., "Chapter 8—Prodrugs and Drug Delivery Systems", The Organic Chemistry of Drug Design and Drug Action, pp. 352-401, 1992.

Thomson, J. et al., "Cellular crosstalk during cholesteric liver injury", Liver Research, vol. 1, No. 1, pp. 26-33, 2017.

Wolff, M., "Some Considerations for Prodrug Design", Burger's Medicinal Chemistry and Drug Discovery, Fifth Edition, vol. I: Principles and Practice, pp. 975-977, 1995.

Office Action received in Canadian Application No. 2,886,676, dated Sep. 23, 2015 in 3 pages.

Office Action received in Canadian Application No. 2,886,676, dated Mar. 21, 2017 in 3 pages.

Office Action received in Canadian Application No. 2,886,676, dated Dec. 1, 2017 in 3 pages.

European Search Report received in related EP Application No. 11167731, dated Nov. 7, 2011 in 9 pages.

Communication Pursuant to Rules 161(1) and 162 EPC in EP Application No. 12 730 164.6, dated Feb. 5, 2015 in 2 pages.

Office Action received in European Application No. 12 730 164.6, dated Jan. 23, 2018 in 4 pages.

Restriction Requirement received in U.S. Appl. No. 14/403,168, dated Jan. 13, 2016 in 6 pages.

Office Action received in U.S. Appl. No. 14/403,168, dated May 24, 2016 in 9 pages.

Office Action received in U.S. Appl. No. 14/403,168, dated Oct. 31, 2016 in 8 pages.

Advisory Action received in U.S. Appl. No. 14/403,168, dated Mar. 6, 2017 in 3 pages.

Notice of Allowance received in U.S. Appl. No. 14/403,168, dated Apr. 28, 2017 in 8 pages.

Restriction Requirement received in U.S. Appl. No. 15/694,303, dated Apr. 23, 2018 in 7 pages.

Office Action received in U.S. Appl. No. 15/694,303, dated Jul. 19, 2018 in 15 pages.

International Search Report and Written Opinion received in PCT Application No. PCT/EP2012/059810, dated Oct. 1, 2012 in 13 pages.

International Preliminary Report on Patentability and Written Opinion received in PCT Application No. PCT/EP2012/059810, dated Dec. 5, 2013 in 10 pages.

Office Action received in Canadian Application No. 2,886,683, dated Sep. 22, 2015 in 7 pages.

Office Action received in Canadian Application No. 2,886,683, dated Jun. 10, 2016 in 7 pages.

European Search Report received in related EP Application No. 11167752, dated Nov. 7, 2011 in 10 pages.

Office Action received in European Application No. 12 729 377.7, dated Dec. 1, 2017 in 4 pages.

Restriction Requirement received in U.S. Appl. No. 14/403,167, dated Mar. 3, 2016 in 9 pages.

Office Action received in U.S. Appl. No. 14/403,167, dated Jun. 28, 2016 in 18 pages.

Office Action received in U.S. Appl. No. 14/403,167, dated Mar. 23, 2017 in 12 pages.

Notice of Allowance received in U.S. Appl. No. 14/403,167, dated Aug. 16, 2017 in 9 pages.

International Search Report and Written Opinion received in PCT Application No. PCT/EP2012/059812, dated Oct. 1, 2012 in 15 pages.

International Preliminary Report on Patentability and Written Opinion received in PCT Application No. PCT/EP2012/059812, dated Dec. 5, 2013 in 11 pages.

(56) References Cited

OTHER PUBLICATIONS

Office Action received in Canadian Application No. 2,887,385, dated Sep. 8, 2015 in 3 pages.
Notice of Allowance received in Canadian Application No, 2,887,385, dated Jun. 20, 2016 in 1 page.
European Search Report received in related EP Application No. 11167741, dated Oct. 20, 2011 in 4 pages.
Restriction Requirement received in U.S. Appl. No. 14/403,166, dated Jan. 14, 2016 in 6 pages.
Office Action received in U.S. Appl. No. 14/403,166, dated May 12, 2016 in 7 pages.
Notice of Allowance received in U.S. Appl. No. 14/403,166, dated Sep. 8, 2016 in 8 pages.
Notice of Allowance received in U.S. Appl. No. 14/403,166, dated Oct. 5, 2016 in 6 pages.
Office Action received in U.S. Appl. No, 15/436,678, dated Jul. 3, 2017 in 6 pages.
Office Action received in U.S. Appl. No. 15/436,678, dated Nov. 14, 2017 in 14 pages.
Notice of Allowance received in U.S. Appl. No. 15/436,678, dated Jul. 27, 2018 in 10 pages.
International Search Report and Written Opinion received in PCT Application No. PCT/EP2012/059813, dated Sep. 26, 2012 in 9 pages.
International Preliminary Report on Patentability and Written Opinion received in PCT Application No. PCT/EP2012/059813, dated Dec. 5, 2013 in 8 pages.
Notice of Allowance dated Aug. 13, 2018 in Canadian Patent Application No. 2,886,676, in 1 Page.
U.S. Appl. No. 16/208,394, filed Dec. 3, 2018, Schlechtingen et al.
Abstract of CAMBRE, "Liquid Detergent Compositions"; HCAPLUS Accession No. 1972:87552, 1 page. This document was cited by the Office as "Year: 1971" in the Office Action dated Jul. 19, 2018 received in U.S. Appl. No. 15/694,303); This document bears a copyright date of 2018, but may have been available in some form at an earlier point in time.
Office Action received in U.S. Appl. No. 15/694,303, dated Jan. 17, 2019.
Germanaud, L. et al., Synthesis of neutral amphiphilic phosphobetaines with variable interionic distances, Bulletin de la Societe Chimique de France, p. 699-704, 1988.
Extended European Search Report, dated Jan. 3, 2020, received in European Application No. 19166502.5.

* cited by examiner

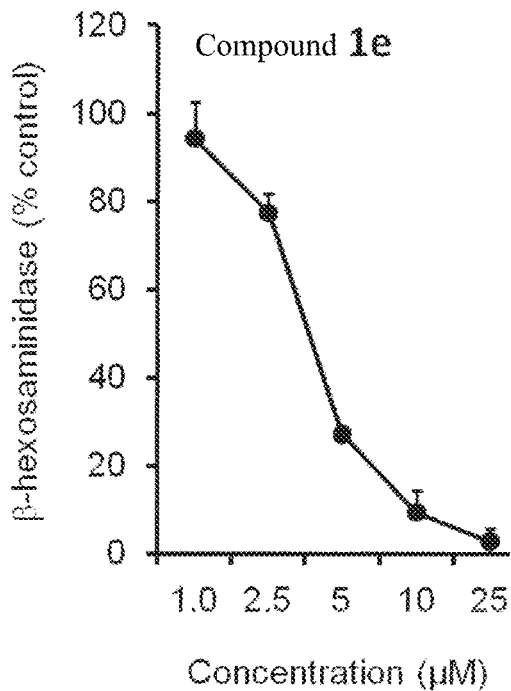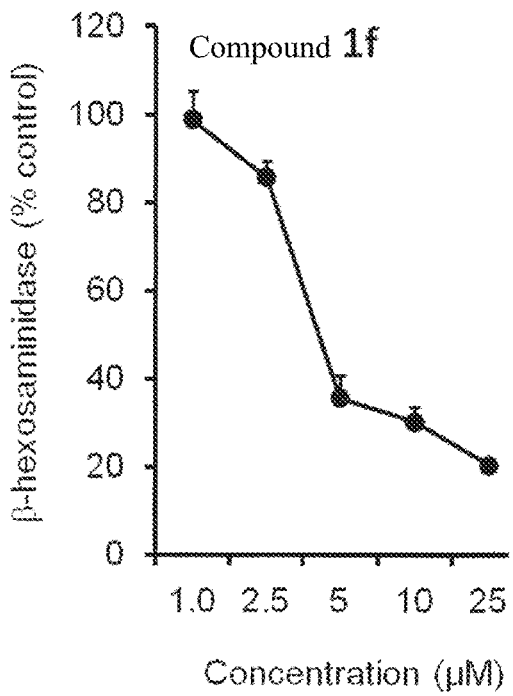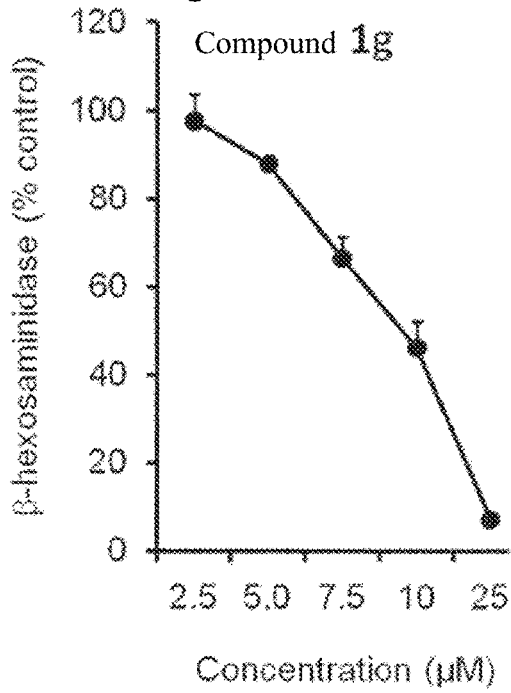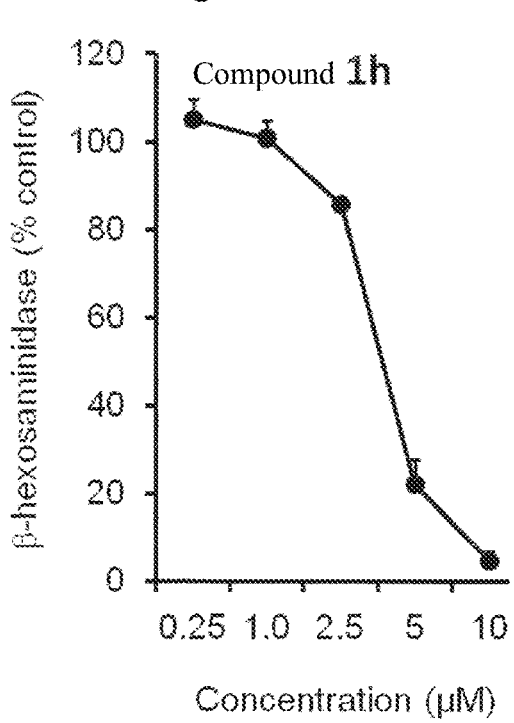

AMINO- OR AMMONIUM-CONTAINING SULFONIC ACID, PHOSPHONIC ACID AND CARBOXYLIC ACID DERIVATIVES AND THEIR MEDICAL USE

This application is a divisional of U.S. patent application Ser. No. 14/403,167, which was filed Apr. 27, 2015, now U.S. Pat. No. 9,850,265, which is a 371 of international application PCT/EP2012/059812 filed May 25, 2012, which claims priority to and the benefit of EP 11167752.2 filed May 26, 2011, the entire contents of all of which are incorporated herein by reference.

The present invention relates to amino- or ammonium-containing sulfonic acid, phosphonic acid and carboxylic acid derivatives, in particular the compounds of formula 1, 2, 3, 4, 5 or 6, and their medical use, including their use in the treatment, prevention or amelioration of an inflammatory, autoimmune and/or allergic disorder.

Without being bound by theory, the compounds provided herein are considered to exert their pharmacological activity through inhibition of the phosphoinositide 3-kinase (PI3K)/Akt kinase pathway. The serine/threonine protein kinase Akt (also known as Protein Kinase B) is a key mediator of signal transduction. Akt is activated by numerous receptors, including those of growth factors, cytokines, hormones and insulin as well as by the attachment of cells to the extracellular matrix. Once activated, the plasma membrane receptors stimulate the activity of PI3K to generate phosphatidylinositol-3,4,5-trisphosphate (PIP3), a lipid second messenger essential for the translocation of Akt, which contains a PIP3-binding pleckstrin homology (PH)-domain, from the cytoplasm to the plasma membrane (Franke et al., Cell 81:727-736, (1995)). Once recruited to the membrane, it is phosphorylated and activated by other kinases (Hemmings, Science 275:628-630 (1997); Hemmlngs, Science 276:534 (1997); Downward, Science 279:673-674 (1998); Alessi et al., EMBO J. 15:6541-6551 (1996)), such as PDK1 and mTORC2.

Akt in turn is responsible for regulating the function of many cellular proteins involved in processes such as transcription and apoptosis (programmed cell death), angiogenesis, cell motility and glucose metabolism (Kulik et al., Mol Cell Biol. 17:1595-1606 (1997); Franke et al., Cell 88:435-437 (1997); Kaufmann-Zeh et al., Nature 385:544-548 (1997) Hemmings, Science 275:628-630 (1997); Dudek et al., Science 275:661-665 (1997)).

These findings indicate that Akt may be a drug target for the treatment of inflammation, autoimmune diseases and allergy. Accordingly, the compounds provided herein, in particular the compounds of formula 1, 2, 3, 4, 5 or 6, are useful in the treatment, prevention or amelioration of such illnesses.

Broad-acting immunomodulatory drugs such as corticosteroids, calcineurin inhibitors and cyclosporin are highly effective and have been used for the therapy of allergic and cellular inflammatory diseases, including autoimmune diseases, for many years. They are potent in suppressing both Th1 and Th2 driven processes, yet they suffer from undesirable side-effects, which limit their therapeutic window. Corticosteroids regulate the expression of numerous genes and, consequently, their use is limited by severe adverse effects. Typical serious adverse effects of short-term corticosteroids use are disturbances in water and salt retention, lipid metabolism, skin thinning and changes in behaviour. More serious adverse effects associated with long-term systemic exposure to corticosteroids include increased appetite and weight gain, deposits of fat in chest, face, upper back, and stomach, water and salt retention leading to swelling and edema, high blood pressure, diabetes, slowed healing of wounds, osteoporosis, cataracts, acne, muscle weakness, thinning of the skin, increased susceptibility to infection, stomach ulcers, increased sweating, mood swings, psychological problems such as depression, adrenal suppression and crisis.

More specifically targeted therapeutics, such as biologies, e.g., antibodies against certain cytokines or their receptors, inhibit a single protein target and are effective in certain situations, but only address one of the targets in a highly redundant inflammatory cascade and are hence often used in combination therapy, as effective resolution of inflammatory diseases requires several targets to be addressed simultaneously.

There is a high unmet medical need for new drugs that curb the underlying disease processes. For instance, in rheumatoid arthritis (RA) such disease-modifying antirheumatic drugs (DMARDs) can slow down progressive joint destruction reducing long-term disease severity. This provides both therapeutic and economic advantages by shortening the therapeutic period and reducing the dose of concomitant medications.

Many chronic inflammatory diseases, including autoimmune diseases such as rheumatoid arthritis (RA), are associated with deregulated intracellular signal transduction pathways, including the phosphoinositide 3-kinase (PI3K)/Akt kinase pathway, and the resultant pathogenic interactions between immune and connective tissue stromal cells lead to changes in cell activation, proliferation, migratory capacity, and cell survival that contribute to inflammation (Tas et aL, Curr Pharm Des. 11:581-611 (2005)). For example, abnormal functioning, differentiation and/or activation of T-ceils, B-cells and myeloid cells have been documented in various autoimmune diseases, including rheumatoid arthritis (RA), diabetes mellitus, lupus and multiple sclerosis and studies have detailed anomalous activation of the Akt signalling axis in the context of systemic autoimmunity (Wu et al., Disord Drug Targets. 9:145-50 (2009)).

Akt is an important signal transduction pathway mediating the delay of neutrophil apoplosis by inflammatory mediators, during neutrophil activation during inflammation (Rane and Klein, Front Biosci. 14:2400-12 (2009)) and control over neutrophil and macrophage migration and apoptosis is a key factor in the pathogenesis of the majority of chronic inflammatory diseases.

RA is a chronic inflammatory disease, which results in inflammation of the synovial lining and destruction of the adjacent bone and cartilage. Synovial macrophages, fibroblasts and lymphocytes are critical to the pathogenesis of this disease, in which apoptosis plays divergent roles. Signaling pathways, such as PI3K/Akt, are highly activated in the RA joint, contributing to the expression of genes that cause inflammation and destruction and expression of a variety of anti-apoptotic molecules. Induction of apoptosis of macrophages, synovial fibroblasts or lymphocytes, through inhibition of the expression of anti-apoptotic molecules, could be therapeutically beneficial in RA (Liu and Pope, Curr Opin Pharmacol. 3:317-22 (2003)). Furthermore, results suggest that signal transduction pathways dependent on PI3K/Akt are involved in the overproduction of the key inflammatory cytokine IL-17 in patients with rheumatoid arthritis (Kim et al., Arthritis Res Ther. 7:R139-148 (2005)).

Akt is closely associated with key membrane-bound receptors and represents a convergent integration point for multiple stimuli implicated in COPD pathogenesis. Akt is also implicated in the systemic manifestations of COPD such as skeletal muscle wasting and metabolic disturbances. As such, Akt represents a particularly attractive therapeutic target for the treatment of COPD (Bozinovski et al, fnt J Chron Obstruct Pulmon Dis. 1:31-38 (2006)).

The compounds provided herein are positioned to be disease-modifying drugs. The compounds have potential for application in a wide variety of chronic inflammatory indications and in combination with a favorable tolerability, the products can be expected to gain adoption by a significant number of patients suffering from the severe side effects of current treatments. Furthermore, the compounds provided herein will be suitable not only for monotherapy but also in combination with existing therapies, which address specific disease targets but are not sufficient to resolve the disease alone.

Activation of the PI3K/Akt pathway is essential for insulin-induced glucose metabolism, including translocation of GLUT4 transported to the cell surface, glucose uptake, glycogen synthesis, suppression of glucose output and triglyceride synthesis as well as insulin-induced mitogenesis (Asano et al., Bioi Pharm Bull. 30:1610-6 (2007)). Hence, inhibitors of PI3K/Akt signalling have potential for use in the treatment of diabetes and obesity (Huang et al., Obes Rev. 10:610-616 (2009)).

WO 2007/071402 describes the use of certain inner ionic phospholipids, phosphonolipids and phosphate derivatives for treatment or prevention of allergic diseases.

Furthermore, specific quaternary ammonium compounds are disclosed in U.S. Pat. Nos. 5,545,667 and 6,136,857 to be useful as antineoplastic agents. Coy E A et al. Int *J immunopharrnacol.* 1990; 12(8):871-81 report a generalized antiproliferative activity of specific amphiphilic molecules on T-Iymphocytes and on a variety of tumor cell lines and a lack of specificity for the immune system. WO 2009/136396 relates to certain sulfobetaines to be used in the treatment of cancer, obesity, age-related macular degeneration and neurodegenerative diseases. WO 92/16201 relates to the use of specific betaine compounds for the treatment of certain viral infections. Yan L, et al. *Bioorg Med Chem Lett* 2004; 14(19):4861-6 describe certain aminopropyl-phosphonic acid derivatives as agonists of sphingosine-1-phosphate G protein-coupled receptors, Birnie C R, et al. *Antimicrob Agents Chemother.* 2000; 44(9):2514-2517 refer to certain N-alkyl-N,N-dimethyl betaines which are reported to show antimicrobial activity. Chen C K M, et al. *J Med Chem.* 2008; 51(18):55945607 report the X-ray structures of certain bisphosphonates which comprise two phosphonate groups and are thus different from the compounds of the present invention for at least that reason. Rachinskii F Y, et al. *Journal of Applied Chemistry of USSR.* 1968; 41(10):2205-2207 describe specific N-carboxymethyl-azepane derivatives which do not have any substituents on the azepane ring carbon atoms, and report bactericidal activity of these compounds. The compound having the CAS number 23035-15-6 (i.e., 1-(carboxymethyl)hexahydro-1-octadecyl-1H-azepinium chloride) does not have any substituents on its azepane ring carbon atoms either. The compound having the CAS number 761356-67-6 (i.e., 3-methyl-4-(sulfomethyl)-1-(3-sulfopropyl)-1-tetradecylpyrrolidinium inner salt) comprises a sulfomethyl substituent on its pyrrolidine ring and, for at least that reason, is different from the compounds of the invention. Further specific quaternary ammonium compounds are, for example, disclosed in: Ernst R et al. Toxicology. 1980; 15(3):233-42; Speijers G J et al. Vaccine. 1989; 7(4):364-8; Vian L et al. Toxic in Vitro. 1995; 9(2): 185-190; Parris N, et al. *Journal of the American Oil Chemists' Society.* 1973; 50(12):509-512; U.S. Pat. Nos. 3,432,408; 4,085,134; and CN 101456810 A.

It has surprisingly been found that the compounds of the present invention, in particular the compounds of formula 1, 2, 3, 4, 5 or 6 as described and defined herein below, have an advantageously low cytotoxicity. The present invention thus solves the problem of providing therapeutic agents having a favorable toxicity profile which are effective, inter alia, in the treatment, prevention or amelioration of inflammatory, autoimmune and/or allergic disorders.

Accordingly, the present invention provides a compound of the following formula 1

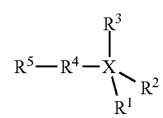

or a pharmaceutical acceptable salt, solvate or prodrug thereof for use in the treatment, prevention or amelioration of an inflammatory, autoimmune and/or allergic disorder, wherein the inflammatory, autoimmune and/or allergic disorder is selected from: psoriasis, atopic dermatitis (atopic eczema), contact dermatitis, xerotic eczema, seborrheic dermatitis, neurodermitis, dyshidrosis, discoid eczema, venous eczema, dermatitis herpetiformis (Duhring's Disease), autoeczematization, dermatomyositis, hyper-IgE (Buckley) syndrome. Wiskott-Aldrich syndrome, anaphylaxis, food allergy, allergic reactions to venomous stings, acute urticarias, chronic urticarias, physical urticarias including aquagenic urticaria, cholinergic urticaria, cold urticaria (chronic cold urticaria), delayed pressure urticaria, dermatographic urticaria, heat urticaria, solar urticaria, vibration urticaria, adrenergic urticaria, urticaria angioedema, inflammatory bowel disease, Crohn's disease, ulcerative colitis, collagenous colitis, lymphocytic colitis, diversion colitis (diverticulitis), Behcet's syndrome, indeterminate colitis, celiac disease, irritable bowel syndrome, post-operative ileus, eosinophilic gastroenteropathy, gastritis, chronic allergic rhinitis, seasonal allergic rhinitis (hay-fever), allergic conjunctivitis, chemical conjunctivitis, neonatal conjunctivitis, Sjögren syndrome, open-angle glaucoma, dry eye disease (DED; including, e.g., aqueous tear-deficient dry eye (ADDE), Sjögren syndrome dry eye (SSDE), non-SSDE, or evaporative dry eye (EDE)), diabetic macular edema (or diabetic retinopathy), chronic obstructive pulmonary disease (COPD), allergic asthma, allergic bronchopulmonary aspergillosis, hypersensitivity pneumonitis, lung fibrosis, rheumatoid arthritis, juvenile rheumatoid arthritis, ankylosing spondylitis, systemic lupus erythematosus (SLE), scleroderma, reactive arthritis, polymyalgia rheumatica, Guillain-Barre syndrome, Hashimoto's thyroiditis, Grave's disease, temporal arteritis, primary biliary cirrhosis, sclerosing cholangitis, autoimmune hepatitis, or alopecia areata.

$R^1$ is a $C_{10-20}$ hydrocarbon group.
$R^2$ is a $C_{1-4}$ alkyl group, and $R^3$ is —H, a $C_{1-4}$ alkyl group or $R^3$ is absent.

Alternatively, $R^2$ and $R^3$ are mutually linked to form a pyrrolidine ring, a piperidine ring or an azepane ring together with the nitrogen atom X to which they are attached, wherein said pyrrolidine ring, said piperidine ring or said azepane ring is optionally substituted with one or more groups independently selected from —OH, —O($C_{1-3}$ alkyl), —O—C(O)—($C_{1-3}$alkyl), alkyl, —C(O)—($C_{1-3}$ alkyl), —C(O)—NH$_2$, —C(O)—NH(C$_{1-3}$alkyl), —C(O)—N(C$_{1-3}$ alkyl)(C$_{1-3}$ alkyl), —NH$_2$, —NH(C$_{1-3}$ alkyl), —N(C$_{1-3}$ alkyl)(C$_{1-3}$ alkyl), —NH—C(O)—(C$_{1-3}$ alkyl), —N(C$_{1-3}$ alkyl)-C(O)—(C$_{1-3}$ alkyl), —NH—C(O)—O(C$_{1-3}$ alkyl) or —N(C$_{1-3}$ alkyl)-C(O)—O(C$_{1-3}$ alkyl).

R$^4$ is a C$_{1-6}$ alkylene group.

R$^5$ is —SO$_3$, —SO$_3$H, —PO$_3^{2-}$, —PO$_3$H$_2$, —PO$_2$(OC$_{1-3}$ alkyl), —PO$_2$H(OC$_{1-3}$alkyl), —PO(OC$_{1-3}$ alkyl)$_2$, —CO$_2$, —CO$_2$H or —CO$_2$(C$_{1-3}$ alkyl).

X is N$^+$ or, if R$^3$ is absent, X is N.

The present invention further relates to a pharmaceutical composition comprising a compound of formula 1, as described and defined herein, or a pharmaceutical acceptable salt, solvate or prodrug thereof, and a pharmaceutical acceptable excipient for use in the treatment, prevention or amelioration of an inflammatory, autoimmune and/or allergic disorder selected from: psoriasis, atopic dermatitis (atopic eczema), contact dermatitis, xerotic eczema, seborrheic dermatitis, neurodermitis, dyshidrosis, discoid eczema, venous eczema, dermatitis herpetiformis (Duhring's Disease), autoeczematization, dermatomyositis, hyper-IgE (Buckley) syndrome. Wiskott-Aldrich syndrome, anaphylaxis, food allergy, allergic reactions to venomous stings, acute urticarias, chronic urticarias, physical urticarias including aquagenic urticaria, cholinergic urticaria, cold urticaria (chronic cold urticaria), delayed pressure urticaria, dermatographic urticaria, heat urticaria, solar urticaria, vibration urticaria, adrenergic urticaria, urticaria angioedema, inflammatory bowel disease, Crohn's disease, ulcerative colitis, collagenous colitis, lymphocytic colitis, diversion colitis (diverticulitis). Behcet's syndrome, indeterminate colitis, celiac disease, irritable bowel syndrome, post-operative ileus, eosinophilic gastroenteropathy, gastritis, chronic allergic rhinitis, seasonal allergic rhinitis (hayfever), allergic conjunctivitis, chemical conjunctivitis, neonatal conjunctivitis, Sjögren syndrome, open-angle glaucoma, dry eye disease (DED; including, e.g., aqueous tear-deficient dry eye (ADDE). Sjögren syndrome dry eye (SSDE), non-SSDE, or evaporative dry eye (EDE)), diabetic macular edema (or diabetic retinopathy), chronic obstructive pulmonary disease (COPD), allergic asthma, allergic bronchopulmonary aspergillosis, hypersensitivity pneumonitis, lung fibrosis, rheumatoid arthritis, juvenile rheumatoid arthritis, ankylosing spondylitis, systemic lupus erythematosus (SLE), scleroderma, reactive arthritis, polymyalgia rheum atica, Guillain-Barre syndrome, Hashimoto's thyroiditis, Grave's disease, temporal arteritis, primary biliary cirrhosis, sclerosing cholangitis, autoimmune hepatitis, or alopecia areata.

Moreover, the present invention relates to a method of treating, preventing or ameliorating an inflammatory, autoimmune and/or allergic disorder, the method comprising the administration of a compound of formula 1, as described and defined herein, or a pharmaceutically acceptable salt, solvate or prodrug thereof, or a pharmaceutical composition comprising any of the aforementioned entities and a pharmaceutically acceptable excipient, to a subject (preferably, a human or a non-human mammal) in need of such a treatment, prevention or amelioration, wherein the inflammatory, autoimmune and/or allergic disorder is selected from: psoriasis, atopic dermatitis (atopic eczema), contact dermatitis, xerotic eczema, seborrheic dermatitis, neurodermitis, dyshidrosis, discoid eczema, venous eczema, dermatitis herpetiformis (Duhring's Disease), autoeczematization, dermatomyositis, hyper-IgE (Buckley) syndrome, Wiskott-Aldrich syndrome, anaphylaxis, food allergy, allergic reactions to venomous stings, acute urticarias, chronic urticarias, physical urticarias including aquagenic urticaria, cholinergic urticaria, cold urticaria (chronic cold urticaria), delayed pressure urticaria, dermatographic urticaria, heat urticaria, solar urticaria, vibration urticaria, adrenergic urticaria, urticaria angioedema, inflammatory bowel disease, Crohn's disease, ulcerative colitis, collagenous colitis, lymphocytic colitis, diversion colitis (diverticulitis). Behcet's syndrome, indeterminate colitis, celiac disease, irritable bowel syndrome, post-operative ileus, eosinophilic gastroenteropathy, gastritis, chronic allergic rhinitis, seasonal allergic rhinitis (hayfever), allergic conjunctivitis, chemical conjunctivitis, neonatal conjunctivitis, Sjögren syndrome, open-angle glaucoma, dry eye disease (DED; including, e.g., aqueous lear-deficienl dry eye (ADDE), Sjögren syndrome dry eye (SSDE), non-SSDE, or evaporative dry eye (EDE)), diabetic macular edema (or diabetic retinopathy), chronic obstructive pulmonary disease (COPD), allergic asthma, allergic bronchopulmonary aspergillosis, hypersensitivity pneumonitis, lung fibrosis, rheumatoid arthritis, juvenile rheumatoid arthritis, ankylosing spondylitis, systemic lupus erythematosus (SLE), scleroderma, reactive arthritis, polymyalgia rheumatica, Guillain-Barre syndrome, Hashimoto's thyroiditis, Grave's disease, temporal arteritis, primary biliary cirrhosis, sclerosing cholangitis, autoimmune hepatitis, or alopecia areata.

Allergic and inflammatory responses are characterized by dynamic interactions of immune and non-immune cells, coordinated through cell-cell contact and soluble immune mediators. These responses and their outcomes are further modified by each individual's genetics and lifestyle.

T helper cells play a key role in initiation and maintenance of inflammatory responses and can be divided into Th1 (cell-mediated immunity) and Th2 (antibody-mediated immunity) driven processes. Imbalances in these responses can result in pathological hyper- or hyposensitivity to antigens. A chronic inflammation manifests (n diverse disease states such as, for instance, inflammatory bowel disease, rheumatoid arthritis, atopic dermatitis, urticaria and psoriasis.

Inflammatory responses to antigens can take the form of helper T cell driven responses of different types. Th1 cells mediate cellular responses involving cytotoxic cells such as macrophages, neutrophils and eosinophils, whereas Th2 cells mediate humoral responses involving secretion of antibodies from B cells and activation of mast cells. Other non-immune responses, such as those involving cyclooxygenase and lipoxygenase may also be involved. Uncontrolled release of cytokines and chemokines is at the heart of inflammatory diseases, like inflammatory bowel disease, rheumatoid arthritis, atopic dermatitis, urticaria and psoriasis.

A new interventional strategy is provided by the compounds according to the present invention, in particular the compounds of formula 1, 2, 3, 4, 5 or 6 as described and defined herein, which broadly modulate the activities of proteins within the inflammatory cascade. Through enrichment of the drug in membrane domains, an allosteric inhibition is exerted on key target proteins in signal transduction cascades in inflammation.

The compounds of the present invention were identified as potent inhibitors of immune mediator release in vitro in a mast cells model, as also demonstrated in Example 27. Furthermore, they inhibited release of the proinflammatory cytokines, TNF-α and interleukin-6 from peripheral blood mononuclear cells (PBMCs) stimulated with lipopolysaccharide, demonstrating immunomodulatory activity in different cell types.

Broad anti-inflammatory activity was confirmed in animal models of Th1 and Th2 driven inflammation. In a predominantly Th1-driven delayed type hypersensitivity (DTH) model in mice, the compounds suppressed the inflammatory response to an extent equivalent to dexamethasone, a marketed corticosteroid characterized by severe side effects, as shown in Example 29. In a predominantly Th2 driven allergic contact dermatitis model, the compounds were highly active after topical application, as shown in Example 30, and also showed an anti-inflammatory effect after oral administration.

In the context of the present invention, it was surprisingly found that the compounds of formula 1, 2, 3, 4, 5 or 6 as described and defined herein are potent inhibitors of mast cell degranulation and thus function as mast cell stabilizers and/or potent inhibitors of allergic and/or cellular inflammation. In particular, it was surprisingly found that the compounds as disclosed herein can be used therapeutically in the treatment, prevention and/or amelioration of immunological disorders and disorders related to allergic and/or cellular inflammation, in particular inflammatory, autoimmune and/or allergic disorders.

T helper (Th) cells are a subgroup of lymphocytes that play an important role in the immune system due to their participation in activating and directing other immune cells. The other major types of lymphocytes are B cells and natural killer (NK) cells. During the antigenic activation and proliferation of Th cells, the Th0 cells differentiate into Th1, Th2 or other subtypes depending on the type of antigen, the antigen presenting cell and the cytokine environment.

Delayed type hypersensitivity, also called type IV hypersensitivity is an antibody-independent Th cell-mediated immune memory response resulting from an over-stimulation of immune cells, commonly lymphocytes and macrophages, resulting in chronic inflammation and cytokine release. Important disease examples are contact dermatitis, chronic inflammation of ileum and colon, e.g. as seen in inflammatory bowel disease (IBD), rheumatoid arthritis and related diseases, ankylosing spondylitis, systemic lupus erythematosus, scleroderma, Gaucher's disease, fibromyalgia, osteoarthritis, reactive arthritis, pelvic inflammatory disease, polymyalgia rheumatica, multiple sclerosis, Guillain-Barre syndrome, Hashimoto's thyroiditis, Grave's disease and chronic transplant rejection. For IBD, for instance. Hue et al. demonstrated a causal relationship between the disease and T cell-mediated intestinal inflammation (Hue, S; et al. (2006) J. Exp. Med. 203 (11), 2473).

Psoriasis is a chronic autoimmune disease affecting the skin. One hypothesis for the cause of psoriasis sees the disease as being an immune-mediated disorder in which the excessive reproduction of skin cells is secondary to factors produced by the immune system. T cells become active, migrate to the dermis and trigger the release of cytokines which cause inflammation and the rapid production of skin cells.

Mast cells, or mastocytes, play a key role in the inflammatory process. When activated, the mast cell rapidly releases its characteristic granules and various hormonal mediators into the the interstitium, a process called degranulation. The molecules released into the extracellular environment include preformed mediators, e.g. histamine and serotonin, newly formed lipid mediators (eicosanoids) and cytokines. In allergic reactions, mast cells remain inactive until an allergen binds to the IgE receptor expressed at the cell surface, leading to degranulation and release of mediators.

Many forms of cutaneous and mucosal allergies, in most cases accompanied by inflammatory symptoms, are mediated largely by mast cells. They play a central role in asthma, eczema, itch and the various forms of rhinitis, conjunctivitis and urticaria. Mast cells are also implicated in the pathology associated with disorders such as rheumatoid arthritis, bullous pemphigoid and multiple sclerosis. They have been shown to be involved in the recruitment of inflammatory cells to the joints and skin. Moreover, mastocytosis is a disorder featuring proliferation of mast cells and exists in a cutaneous and systemic form.

Atopic dermatitis, also known as neurodermitis, is an inflammatory and pruritic skin disorder characterised by chronic inflammation. Although the causes underlying atopic dermatitis are not well understood and the relationships between intake of, or contact with, allergens and various inflammatory stimuli are not well established, it is postulated that mast cell and/or T cell-related processes are involved in the pathological processes leading to atopic dermatitis.

Asthma and chronic obstructive pulmonary disease (COPD) are both obstructive airway disorders, but differing types of inflammation are involved in the pathogenesis of these diseases. Asthma is frequently an allergic process with a preponderance of Th2 cells and eosinophils in the airways. In contrast, there is predominant Th1 activity in the blood of COPD patients (Lecki, M J; et al. (2003) Thorax 58, 23).

Dry eye disease (DED) is an inflammatory disorder of the lacrimal functional unit leading to chronic ocular surface disease, impaired quality of vision, and a wide range of complications. It is recognized that a chronic inflammatory response plays a key role in the pathogenesis of human dry eye disease (Calonge M, et al. Ocul Immunol Inflamm. 2010. 18:244-253; Stevenson W, et al. Arch Ophthalmol. 2012. 130:90-100; Zoukhri D. Exp Eye Res. 2006. 82:885-898; Pflugfelder S C. Am J Ophthalmol. 2004. 137:337-342).

Diabetic macular edema (or diabetic retinopathy) is characterized by early retinal microvascular dysfunction and is a leading cause of blindness in subjects suffering from diabetes. There is evidence indicating that retinal inflammation plays an important role in the pathogenesis of diabetic macular edema (Joussen A M, et al. FASEBJ. 2004. 18:1450-1452; Rangasamy S, et al. Middle East Afr J Ophthalmol. 2012. 19:52-59; Meleth A D, et al. Invest Ophthalmol Vis Sci. 2005. 46:4295-4301; Funatsu H, et al. Ophthalmology. 2009. 116:73-79; Kim S J, et al. Surv Ophthalmol. 2010. 55:108-133).

Accordingly, the compounds of the present invention, in particular the compounds of formula 1, 2, 3, 4, 5 or 6, are useful in the treatment, prevention or amelioration of an inflammatory, autoimmune and/or allergic disorder.

The inflammatory, autoimmune and/or allergic disorder to be treated, prevented or ameliorated using the compounds of formula 1 or 2 according to the invention is selected from: psoriasis, atopic dermatitis (atopic eczema), contact dermatitis, xerotic eczema, seborrheic dermatitis, neurodermitis, dyshidrosis, discoid eczema, venous eczema, dermatitis herpetiformis (Duhring's Disease), autoeczematization, dermatomyositis, hyper-IgE (Buckley) syndrome, Wiskott-Aldrich syndrome, anaphylaxis, food allergy, or allergic reactions to venomous stings; acute urticarias, chronic urticarias, physical urticarias including aquagenic urticaria, cholinergic urticaria, cold urticaria (chronic cold urticaria), delayed pressure urticaria, dermatographic urticaria, heat urticaria, solar urticaria, vibration urticaria, adrenergic urticaria, or urticaria angioedema; inflammatory bowel disease, Crohn's disease, ulcerative colitis, collagenous colitis, lymphocytic colitis, diversion colitis (diverticulitis), Behcet's syndrome, indeterminate colitis, celiac disease, irritable bowel syndrome, post-operative ileus, eosinophilic gastroenteropathy, or gastritis; chronic allergic rhinitis, seasonal allergic rhinitis (hay-fever), allergic conjunctivitis, chemical conjunctivitis, neonatal conjunctivitis. Sjögren syndrome, open-angle glaucoma, dry eye disease (DED; including, e.g., aqueous tear-deficient dry eye (ADDE), Sjögren syndrome dry eye (SSDE), non-SSDE, or evaporative dry eye (EDE)), or diabetic macular edema (or diabetic retinopathy); chronic obstructive pulmonary disease (COPO), allergic asthma, allergic bronchopulmonary aspergillosis, hypersensitivity pneumonitis, or lung fibrosis; rheumatoid arthritis, juvenile rheumatoid arthritis, ankylosing spondylitis, systemic lupus erythematosus (SLE), scleroderma, reactive arthritis, or polymyalgia rheumatica; or Guillain-Barre syndrome, Hashimoto's thyroiditis, Grave's disease, temporal arteritis, primary biliary cirrhosis, sclerosing cholangitis, autoimmune hepatitis, or alopecia areata.

The efficacy of the compounds of the present invention, in particular the compounds of formula 1, 2, 3, 4, 5 or 6, in the inhibition of Akt kinase activation has furthermore been demonstrated in Example 28.

The compounds of the invention, which have been demonstrated to exhibit an efficacy in the suppression of the inflammatory response at least equivalent to that of the corticosteroid dexamethasone, as also shown in Example 29, are furthermore advantageous in that they do not show the adverse effects which are usually observed for corticosteroids, such as reduction of lymph node weight and cell number (Example 30), which makes them particularly useful in the treatment, prevention or amelioration of inflammatory, autoimmune and/or allergic disorders.

Moreover, the compounds of the present invention, including the compounds of formula 1, 2, 3, 4, 5 or 6, have a particularly low cytotoxicity and, thus, an advantageous toxicity profile, as also demonstrated in Example 27.

The compound of formula 1 as defined above is described in more detail in the following.

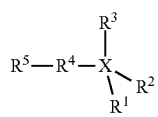

1

$R^1$ is a $C_{10-20}$ hydrocarbon group. Preferably, $R^1$ is an alkyl group, an alkenyl group, or an alkynyl group; more preferably, $R^1$ is a linear alkyl group, a linear alkenyl group, or a linear alkynyl group; even more preferably, $R^1$ is a linear alkyl group. The number of carbon atoms of the hydrocarbon group, the alkyl group, the alkenyl group, or the alkynyl group is 10 to 20, preferably 12, 14 or 16. Accordingly, it is particularly preferred that $R^1$ is —$(CH_2)_{11}$—$CH_3$, —$(CH_2)_{13}$—$CH_3$, or —$(CH_2)_{15}$—$CH_3$.

$R^2$ is a $C_{1-4}$ alkyl group, and $R^3$ is —H, a alkyl group or $R^3$ is absent; or $R^2$ and $R^3$ are mutually linked to form a pyrrolidine ring, a piperidine ring or an azepane ring together with the nitrogen atom X to which they are attached, wherein said pyrrolidine ring, said piperidine ring or said azepane ring is optionally substituted with one or more groups independently selected from —OH, —$O(C_{1-3}$ alkyl), —O—C(O)—$(C_{1-3}$ alkyl), $C_{1-3}$ alkyl, —$NH_2$, —NH$(C_{1-3}$ alkyl) or —N$(C_{1-3}$ alkyl)$(C_{1-3}$ alkyl).

In one preferred embodiment, $R^2$ is methyl, and $R^3$ is —H, a $C_{1-4}$ alkyl group or $R^3$ is absent. More preferably, $R^2$ is methyl, and $R^3$ is —H, methyl or $R^3$ is absent. Even more preferably, $R^2$ is methyl and $R^3$ is methyl.

In another preferred embodiment, $R^2$ and $R^3$ are mutually linked to form a pyrrolidine ring, a piperidine ring or an azepane ring together with the nitrogen atom X to which they are attached. More preferably, $R^2$ and $R^3$ are mutually linked to form a piperidine ring together with the nitrogen atom X to which they are attached. The pyrrolidine ring, the piperidine ring or the azepane ring may be substituted with one or more (such as, e.g., one, two, three, or four), preferably one or two, more preferably one, groups independently selected from —OH, —$O(C_{1-3}$ alkyl), —O—C(O)—$(C_{1-3}$ alkyl), $C_{1-3}$ alkyl, —C(O)—$(C_{1-3}$ alkyl), —C(O)—$NH_2$, —C(O)—NH$(C_{1-3}$ alkyl), —C(O)—N$(C_{1-3}$ alkyl)$(C_{1-3}$ alkyl), —$NH_2$, —NH$(C_{1-3}$ alkyl), —N$(C_{1-3}$ alkyl)$(C_{1-3}$ alkyl), —NH—C(O)—$(C_{1-3}$ alkyl), —N$(C_{1-3}$ alkyl)-C(O)—$(C_{1-3}$ alkyl), —NH—C(O)—O$(C_{1-3}$ alkyl) or —N$(C_{1-3}$ alkyl), —C(O)—O$(C_{1-3}$ alkyl). Preferably, the pyrrolidine ring, the piperidine ring or the azepane ring is unsubstituted or substituted with one or more (such as, e.g., one, two, three, or four), preferably one or two, more preferably one, groups independently selected from —OH, —$O(C_{1-3}$ alkyl), —O—C(O)—$(C_{1-3}$ alkyl), $C_{1-3}$ alkyl, —C(O)—$NH_2$, —C(O)—NH$(C_{1-3}$ alkyl), —C(O)—N$(C_{1-3}$ alkyl)$(C_{1-3}$ alkyl), —$NH_2$, —NH$(C_{1-3}$ alkyl), or —N$(C_{1-3}$ alkyl)$(C_{1-3}$ alkyl), preferably selected independently from —OH, —$O(C_{1-3}$ alkyl), —O—C(O)—$(C_{1-3}$ alkyl), $C_{1-3}$ alkyl, —$NH_2$, —NH$(C_{1-3}$ alkyl), or —N$(C_{1-3}$ alkyl) $(C_{1-3}$ alkyl). More preferably, the pyrrolidine ring, the piperidine ring or the azepane ring is unsubstituted or substituted with one group selected from —OH, —$O(C_{1-3}$ alkyl), —O—C(O)—$(C_{1-3}$ alkyl), $C_{1-3}$ alkyl, —C(O)—$NH_2$, —C(O)—NH$(C_{1-3}$ alkyl), —C(O)—N$(C_{1-3}$ alkyl)$(C_{1-3}$ alkyl), —$NH_2$, —NH$(C_{1-3}$ alkyl) or —N$(C_{1-3}$ alkyl)$(C_{1-3}$ alkyl). Even more preferably, the pyrrolidine ring, the piperidine ring or the azepane ring is unsubstituted or substituted with one group —OH.

Accordingly, it is particularly preferred that $R^2$ and $R^3$ are mutually linked to form a piperidine ring together with the nitrogen atom X to which they are attached, wherein the piperidine ring is optionally substituted with one group —OH, preferably in para position with respect to the nitrogen atom X.

$R^4$ is a $C_{1-6}$ alkylene group. The alkylene group may be linear or branched; preferably, the alkylene group is linear. The alkylene group has 1 to 6 (i.e., 1, 2, 3, 4, 5 or 6) carbon atoms and preferably has 2 or 3 carbon atoms, more preferably 3 carbon atoms. It is particularly preferred that RA is —$(CH_2)_3$—.

$R^5$ is —$SO_3^-$, —$SO_3H$, —$PO_3H^-$, —$PO_3^{2-}$, —$PO_3H_2$, —$PO_2(OC_{1-3}$ alkyl)$^-$, —$PO_2H(OC_{1-3}$ alkyl), —$PO(OC_{1-3}$ alkyl)$_2$, —$CO_2^-$, —$CO_2H$ or —$CO_2(C_{1-3}$ alkyl). Preferably, $R^5$ is -$SO_3^-$, —$SO_3H$, -$PO_3H^-$, —$PO_3^{2-}$, or —$PO_3H_2$. In one preferred embodiment, $R^5$ is —$SO_3^-$ or —$SO_3H$. In another preferred embodiment, $R^5$ is —$PO_3^{2-}$, —$PO_3H$ or —$PO_3H_2$.

Accordingly, in a particularly preferred embodiment $R^5$ is —$SO_3^-$ or —$SO_3H$ and $R^4$ is a linear or branched alkylene group (preferably, $R^4$ is a linear alkylene group having 2, 3, 4, 5 or 6 carbon atoms; more preferably, $R^4$ is a linear alkylene group having 3 carbon atoms; even more preferably, $R^4$ is —$(CH_2)_3$—). In a further particularly preferred embodiment $R^5$ is —$PO_3^{2-}$, —$PO_3H$ or —$PO_3H_2$ and $R^4$ is a linear or branched $C_{2-6}$ alkylene group (preferably, $R^4$ is a linear alkylene group having 2, 3, 4, 5 or 6 carbon atoms;

more preferably. R⁴ is a linear alkylene group having 3 carbon atoms; even more preferably, R⁴ is —(CH₂)₃—.

X is N⁺ or, if R³ is absent, X is N.

A person skilled in the art understands that, if the compound of formula 1 is provided in solution, the protonation of the acid group R⁵ depends on the pH of the solution. For example, if R⁵ is —PO₃H⁻ it may be present as —PO₃H₂ in a more acidic environment or as —PO₃²⁻ in a more alkaline environment.

Likewise, a skilled person understands that, if the compound of formula 1 is provided in solution and if R³ in formula 1 is —H or is absent, the protonation of the nitrogen atom X and, accordingly, the charge at the nitrogen atom X depends on the pH of the solution. Thus, depending on the pH of the solution, R³ may be —H and X may be N⁺, or R³ may be absent and X may be N.

Preferred examples of the compound of formula 1 are the compounds 1a to 1x shown below or pharmaceutical acceptable salts, solvates or prodrugs thereof:

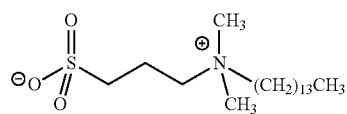

1a

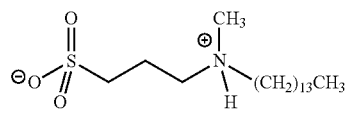

1b

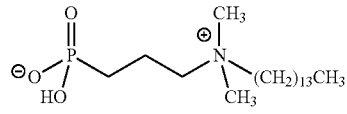

1c

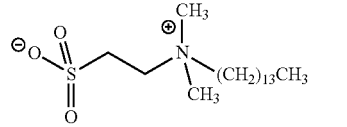

1d

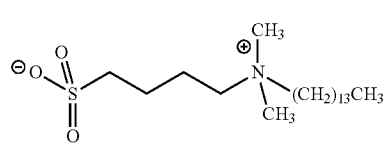

1e

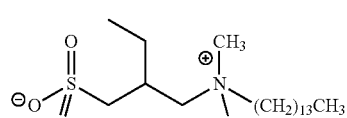

1f

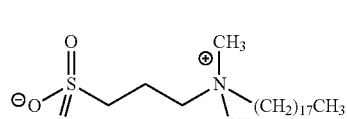

1g

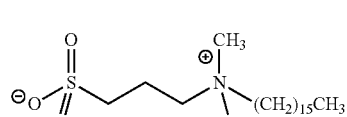

1h

-continued

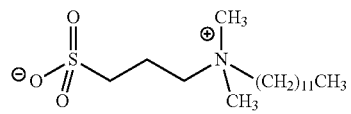

1i

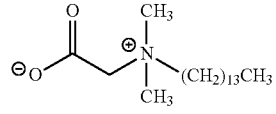

1j

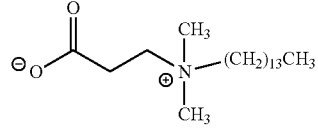

1k

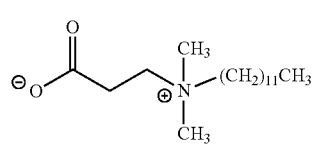

1m

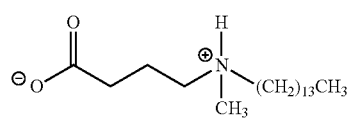

1n

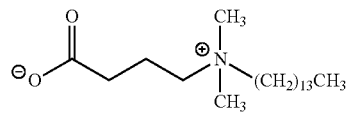

1o

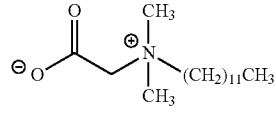

1p

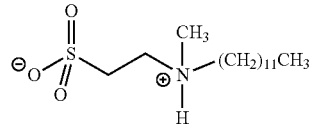

1q

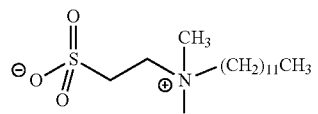

1r

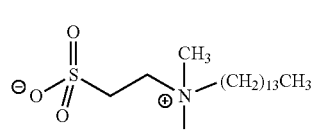

1s

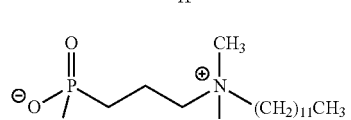

1t

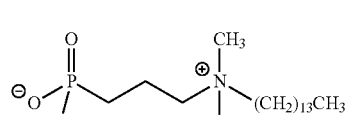

1u

-continued

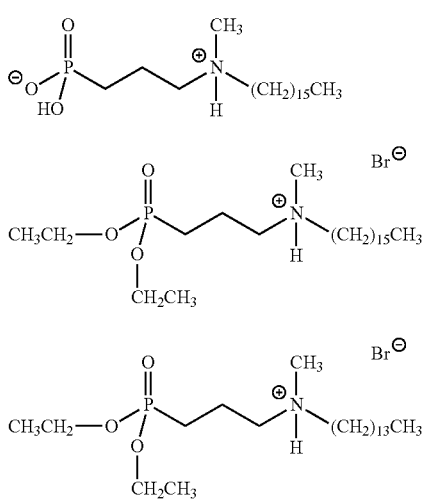

In one embodiment described above, $R^2$ and $R^3$ in formula 1 are mutually linked to form a pyrrolidine ring, a piperidine ring or an azepane ring together with the nitrogen atom X to which they are attached, wherein said pyrrolidine ring, said piperidine ring or said azepane ring is optionally substituted with one or more groups independently selected from —OH, —O($C_{1-3}$ alkyl), —O—C(O)—($C_{1-3}$alkyl), $C_{1-3}$ alkyl, —C(O)—($C_{1-3}$ alkyl), —C(O)—$NH_2$, —C(O)—NH($C_{1-3}$ alkyl), —C(O)—N($C_{1-3}$ alkyl)($C_{1-3}$ alkyl), —$NH_2$, —NH($C_{1-3}$ alkyl), —N($C_{1-3}$ alkyl)($C_{1-3}$ alkyl), —NH—C(O)—($C_{1-3}$ alkyl), —N($C_{1-3}$ alkyl)-C(O)—($C_{1-3}$ alkyl), —NH—C(O)—O($C_{1-3}$ alkyl) or —N($C_{1-3}$ alkyl)-C(O)—O($C_{1-3}$ alkyl).

Accordingly, the compound of formula 1 may be a compound of the following formula 2

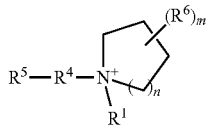

or a pharmaceutical acceptable salt, solvate or prodrug thereof for use in the treatment, prevention or amelioration of an inflammatory, autoimmune and/or allergic disorder.

In formula 2, the groups $R^1$, $R^4$, and $R^5$ have the meanings or the preferred meanings defined herein above for the compound of formula 1.

n is 1, 2, or 3. Preferably, n is 2.

m is an integer from 0 to 4. Preferably, m is 0, 1, or 2; more preferably, m is 0 or 1; even more preferably, m is 1.

Each $R^6$ is independently selected from —OH, —O($C_{1-3}$ alkyl), —O—C(O)—($C_{1-3}$ alkyl), $C_{1-3}$ alkyl, —C(O)—($C_{1-3}$ alkyl), —C(O)—$NH_2$, —C(O)—NH($C_{1-3}$ alkyl), —C(O)—N($C_{1-3}$ alkyl)($C_{1-3}$ alkyl), —$NH_2$, —NH($C_{1-3}$ alkyl), —N($C_{1-3}$ alkyl)($C_{1-3}$ alkyl), —NH—C(O)—($C_{1-3}$ alkyl), —N($C_{1-3}$ alkyl)-C(O)—($C_{1-3}$ alkyl). —NH—C(O)—O($C_{1-3}$ alkyl) or —N($C_{1-3}$ alkyl)-C(O)—O($C_{1-3}$ alkyl). Preferably, each $R^6$ is independently selected from —OH, —O($C_{1-3}$ alkyl), —O—C(O)—($C_{1-3}$ alkyl), $C_{1-3}$ alkyl, —C(O)—$NH_2$, —C(O)—NH($C_{1-3}$ alkyl), —C(O)—N($C_{1-3}$ alkyl)($C_{1-3}$ alkyl), —$NH_2$, —NH($C_{1-3}$ alkyl), or alkyl)($C_{1-3}$ alkyl). More preferably, each $R^6$ is independently selected from —OH, —O($C_{1-3}$ alkyl), —O—C(O)—($C_{1-3}$ alkyl), $C_{1-3}$ alkyl, —$NH_2$, —NH($C_{1-3}$ alkyl) or —N($C_{1-3}$ alkyl)($C_{1-3}$ alkyl). Even more preferably, each $R^6$ is —OH.

It is to be understood that each $R^6$ is attached to a carbon atom of the pyrrolidine, piperidine or azepane ring. It is further to be understood that, if m is 0, the pyrrolidine, piperidine or azepane ring (to which $R^6$ would be attached) is unsubstituted, i.e. is substituted with hydrogen.

In one embodiment, n is 1 or 3, and m is 0.

In a preferred embodiment, n is 2, m is 1, and $R^6$ is —OH, —O($C_{1-3}$ alkyl), —O—C(O)—($C_{1-3}$ alkyl), $C_{1-3}$ alkyl, —$NH_2$, —NH($C_{1-3}$ alkyl) or —N($C_{1-3}$ alkyl)($C_{1-3}$ alkyl), in particular —OH. In this embodiment, it is further preferred that $R^6$ is in para position in respect of the ring nitrogen atom $N^+$.

Preferred examples of the compound of formula 2 are the compounds 2a to 2d shown below or pharmaceutically acceptable salts, solvates or prodrugs thereof:

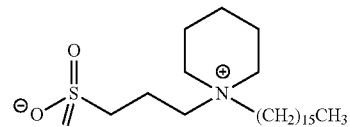

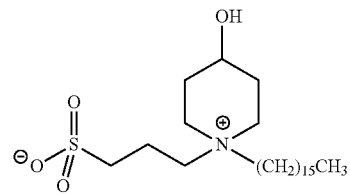

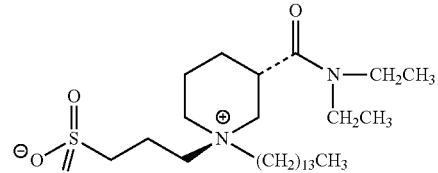

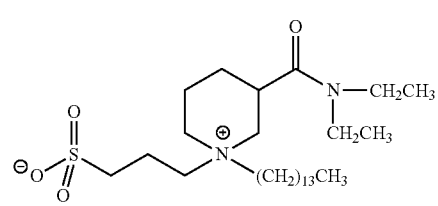

The invention furthermore relates to a compound of formula 3 or a pharmaceutical acceptable salt, solvate or prodrug thereof for use as a medicament.

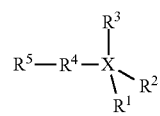

In formula 3, the groups $R^1$ and X have the same meanings and preferred meanings as described and defined herein above for the corresponding groups in formula 1.

$R^2$ in formula 3 is a $C_{1-3}$ alkyl group, and $R^3$ is —H or $R^2$ is absent; or $R^2$ and $R^3$ are mutually linked to form a pyrrolidine ring, a piperidine ring or an azepane ring together with the nitrogen atom X to which they are attached, wherein said pyrrolidine ring, said piperidine ring or said azepane ring is substituted with one or more groups independently selected from —OH, —O($C_{1-3}$ alkyl), —O—C(O$_{1-3}$ alkyl), alkyl, —C(O)—($C_{1-3}$ alkyl), —C(O)—$NH_2$, —C(O)—NH($C_{1-3}$ alkyl), —C(O)—N($C_{1-3}$ alkyl)($C_{1-3}$ alkyl), —$NH_2$, —NH($C_{1-3}$ alkyl), —N($C_{1-3}$ alkyl)($C_{1-3}$ alkyl), —NH—C(O)—($C_{1-3}$ alkyl), —N($C_{1-3}$ alkyl)-C(O)—($C_{1-3}$ alkyl), —NH—C(O)—O($C_{1-3}$ alkyl) or —N($C_{1-3}$ alkyl)-C(O)—O($C_{1-3}$ alkyl).

In one preferred embodiment, $R^2$ is methyl, and $R^3$ is —H or $R^3$ is absent.

In another preferred embodiment, $R^2$ and $R^3$ are mutually linked to form a pyrrolidine ring, a piperidine ring or an azepane ring together with the nitrogen atom X to which they are attached. More preferably, $R^2$ and $R^3$ are mutually linked to form a piperidine ring together with the nitrogen atom X to which they are attached. The pyrrolidine ring, the piperidine ring or the azepane ring is substituted with one or more (such as, e.g., one, two, three, or four), preferably one or two, more preferably one, groups independently selected from —OH, —O($C_{1-3}$ alkyl), —O—C(O)—($C_{1-3}$ alkyl), $C_{1-3}$ alkyl, —C(O)—($C_{1-3}$ alkyl), —C(O)—$NH_2$, —C(O)—NH($C_{1-3}$ alkyl), —C(O)—N($C_{1-3}$ alkyl)($C_{1-3}$ alkyl), —$NH_2$, —NH($C_{1-3}$ alkyl), —N($C_{1-3}$ alkyl)($C_{1-3}$ alkyl), —NH—C(O)—($C_{1-3}$ alkyl), —N($C_{1-3}$ alkyl)-C(O)—($C_{1-3}$ alkyl), —NH—C(O)—O($C_{1-3}$ alkyl) or —N($C_{1-3}$ alkyl)-C(O)—O($C_{1-3}$ alkyl).

Preferably, the pyrrolidine ring, the piperidine ring or the azepane ring is substituted with one or more (such as, e.g., one, two, three, or four), preferably one or two, more preferably one, groups independently selected from —OH, —O($C_{1-3}$ alkyl), —O—C(O)—($C_{1-3}$ alkyl), $C_{1-3}$ alkyl, —C(O)—$NH_2$, —C(O)—NH($C_{1-3}$ alkyl), —C(O)—N($C_{1-3}$ alkyl)($C_{1-3}$ alkyl), —$NH_2$, —NH($C_{1-3}$ alkyl), or —N($C_{1-3}$ alkyl)($C_{1-3}$ alkyl), preferably selected independently from —OH, —O($C_{1-3}$ alkyl), —O—C(O)—($C_{1-3}$ alkyl), $C_{1-3}$ alkyl, —$NH_2$, —NH($C_{1-3}$ alkyl), or —N($C_{1-3}$ alkyl)($C_{1-3}$ alkyl). More preferably, the pyrrolidine ring, the piperidine ring or the azepane ring is substituted with one group selected from —OH, —O($C_{1-3}$ alkyl), —O—C(O)—($C_{1-3}$ alkyl), $C_{1-3}$ alkyl, —C(O)—$NH_2$, —C(O)—NH($C_{1-3}$ alkyl), —C(O)—N($C_{1-3}$ alkyl)($C_{1-3}$ alkyl), —$NH_2$, —NH($C_{1-3}$ alkyl), or —N($C_{1-3}$ alkyl)($C_{1-3}$ alkyl). Even more preferably, the pyrrolidine ring, the piperidine ring or the azepane ring is substituted with one group —OH. Accordingly, it is particularly preferred that $R^2$ and $R^3$ are mutually linked to form a piperidine ring together with the nitrogen atom X to which they are attached, wherein the piperidine ring is substituted with one group —OH, preferably in para position with respect to the nitrogen atom X.

$R^4$ is a $C_{1-6}$ alkylene group. The alkylene group may be linear or branched; preferably, the alkylene group is linear. The alkylene group has 1 to 6 (i.e., 1, 2, 3, 4, 5 or 6) carbon atoms and preferably has 2 or 3 carbon atoms, more preferably 3 carbon atoms. It is particularly preferred that $R^4$ is —$(CH_2)_3$—.

If $R^4$ is an alkylene group having 1, 2, 4, 5 or 6 carbon atoms, then $R^5$ is —$SO_3$, —$SO_3H$, —$PO_3H^-$, —$PO_3^{2-}$, —$PO_3H_2$, —$PO_2(OC_{1-3}$ alkyl)$^-$, —$PO_2H(OC_{1-3}$ alkyl), —$PO(OC_{1-3}$ alkyl)$_2$, —$CO_2^-$, —$CO_2H$, or -$CO_2(C_{1-3}$ alkyl), and preferably is $R^5$ is —$SO_3^-$, —$SO_3H$, —$PO_3H^-$, —$PO_3^{2-}$, or —$PO_3H_2$. If $R^4$ is an alkylene group having 3 carbon atoms, then $R^5$ is —$SO_3$, —$SO_3H$, —$CO_2^-$, —$CO_2H$, —$CO_2(C_{1-3}$ alkyl), —$PO_2(OC_{1-3}$ alkyl), —PO($OC_{1-3}$ alkyl)$_2$, or —PO($OC_{1-3}$ alkyl)$_2$, and preferably $R^5$ is —$SO_3^-$, —$SO_3H$, —$CO_2^-$ or -$CO_2H$, more preferably —$SO_3^-$ or —$SO_3H$.

Accordingly, in a particularly preferred embodiment $R^5$ is —$SO_3$ or —$SO_3H$ and $R^4$ is a linear or branched $C_{2-6}$ alkylene group (preferably, $R^4$ is a linear alkylene group having 2, 3, 4, 5 or 6 carbon atoms; more preferably, $R^4$ is a linear alkylene group having 3 carbon atoms; even more preferably, $R^4$ is —$(CH_2)_3$—). In a further particularly preferred embodiment $R^5$ is —$PO_3^{2-}$, —$PO_3H^-$ or —$PO_3H_2$ and $R^4$ is a linear or branched alkylene group having 2, 4, 5 or 6 carbon atoms (preferably, $R^4$ is a linear alkylene group having 2, 4, 5 or 6 carbon atoms). In a further particularly preferred embodiment, $R^4$ is an alkylene group having 1, 2, 4, 5 or 6 carbon atoms, and $R^5$ is —$PO_3H^-$, —$PO_3^{2-}$, —$PO_3H_2$, —$PO_2(OC_{1-3}$ alkyl)$^-$, —$PO_2H(OC_{1-3}$ alkyl), —PO($OC_{1-3}$ alkyl)$_2$, —$CO_2^-$, —$CO_2H$, or —$CO_2(C_{1-3}$ alkyl); or $R^4$ is an alkylene group having 3 carbon atoms, and $R^5$ is —$CO_2^-$, —$CO_2H$, —$CO_2(C_{1-3}$ alkyl), —$PO_2(OC_{1-3}$ alkyl)$^-$, —$PO_2H(OC_{1-3}$ alkyl), or —PO($OC_{1-3}$ alkyl)$_2$.

Preferred examples of the compound of formula 3 are the compounds 1b, 1n, 1q, 1s, 1w, 1x, 2b, 2c or 2d shown below or pharmaceutical acceptable salts, solvates or prodrugs thereof:

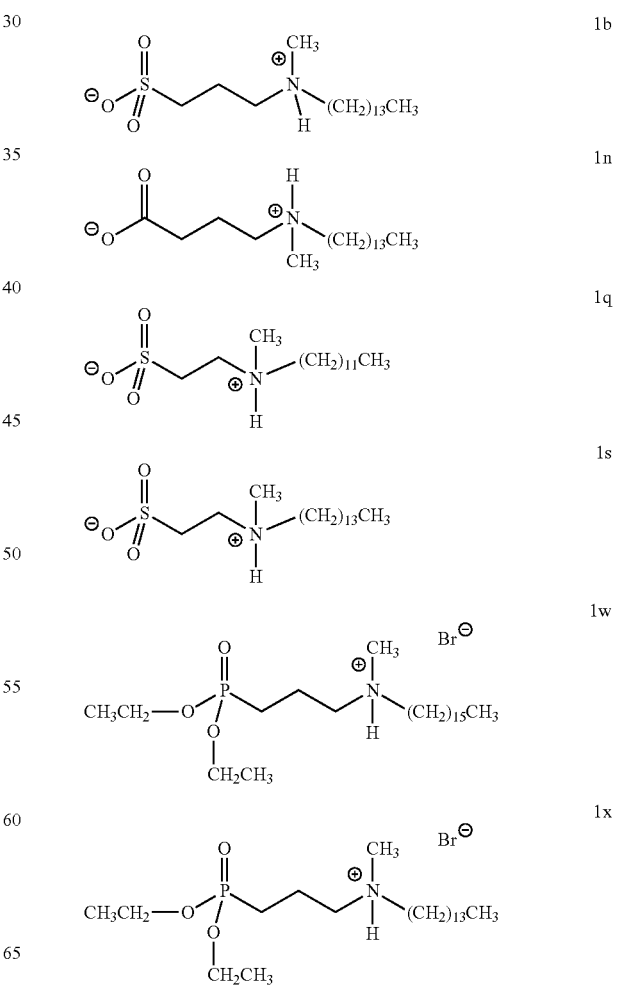

-continued

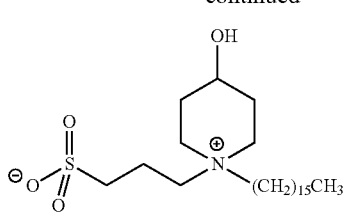

2b

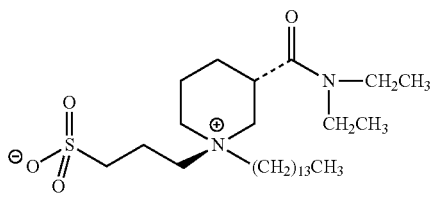

2c

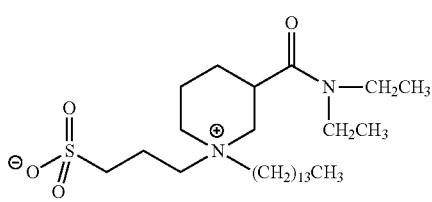

2d

In accordance with the above definition of the compound of formula 3, the groups $R^2$ and $R^3$ may, in one embodiment, be mutually linked to form a pyrrolidine ring, a piperidine ring or an azepane ring together with the nitrogen atom X to which they are attached, wherein said pyrrolidine ring, said piperidine ring or said azepane ring is substituted with one or more groups independently selected from —OH, —O($O_{1-3}$ alkyl), —O—C(O)—($C_{1-3}$ alkyl), $C_{1-3}$ alkyl, —C(O)—($C_{1-3}$ alkyl), —C(O)—$NH_2$, —C(O)—NH($C_{1-3}$ alkyl), —C(O)—N($C_{1-3}$ alkyl)($C_{1-3}$ alkyl), —$NH_2$, —NH($C_{1-3}$ alkyl), —N($C_{1-3}$ alkyl)($C_{1-3}$ alkyl), —NH—C(O)—($C_{1-3}$ alkyl), —N($C_{1-3}$ alkyl)-C(O)—($C_{1-3}$ alkyl), —NH—C(O)—O($C_{1-3}$ alkyl) or —N($C_{1-3}$ alkyl)-C(O)—O($C_{1-3}$ alkyl).

The compound of formula 3, which is provided herein as a medicament, may thus be a compound of the following formula 4

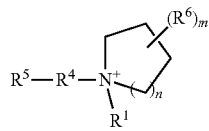

4 or a pharmaceutically acceptable salt, solvate or prodrug thereof.

The groups $R^1$, $R^4$ and $R^5$ in formula 4 have the same meanings and preferred meanings as defined herein above for the corresponding groups in formula 3.

n is 1, 2, or 3. Preferably, n is 2.

In formula 4, m is an integer from 1 to 4. Preferably, m is 1 or 2; more preferably, m is 1.

Each $R^6$ is independently selected from —OH, —O($C_{1-3}$ alkyl), —O—C(O)—($C_{1-3}$ alkyl), $C_{1-3}$ alkyl, —C(O)—($C_{1-3}$ alkyl), —C(O)—$NH_2$, —C(O)—NH($C_{1-3}$ alkyl), —C(O)—N($C_{1-3}$ alkyl)($C_{1-3}$ alkyl), —$NH_2$, —NH($C_{1-3}$ alkyl), —N($C_{1-3}$ alkyl)($C_{1-3}$ alkyl), —NH—C(O)—($C_{1-3}$ alkyl), —N($C_{1-3}$ alkyl)-C(O)—($C_{1-3}$ alkyl), —NH—C(O)—O($C_{1-3}$ alkyl) or —N($C_{1-3}$ alkyl)-C(O)—O($C_{1-3}$ alkyl). Preferably, each $R^6$ is independently selected from —OH, —O($C_{1-3}$ alkyl), —O—C(O)—($C_{1-3}$ alkyl), $C_{1-3}$ alkyl, —C(O)—$NH_2$, —C(O)—NH($C_{1-3}$ alkyl), —C(O)—N($C_{1-3}$ alkyl)($C_{1-3}$ alkyl), —$NH_2$, —NH($C_{1-3}$ alkyl), or —N($C_{1-3}$ alkyl)($C_{1-3}$ alkyl). More preferably, each $R^6$ is independently selected from —OH, —O($C_{1-3}$ alkyl), —O—C(O)—($C_{1-3}$ alkyl), $C_{1-3}$ alkyl, —$NH_2$, —NH($C_{1-3}$ alkyl) or —N($C_{1-3}$ alkyl)($C_{1-3}$ alkyl). Even more preferably, each $R^6$ is —OH.

It is to be understood that each $R^6$ is attached to a carbon atom of the pyrrolidine, piperidine or azepane ring.

In a preferred embodiment, n in formula 4 is 2, m is 1, and $R^6$ is —OH, —O($C_{1-3}$ alkyl), —O—C(O)—($C_{1-3}$ alkyl), $C_{1-3}$ alkyl, —$NH_2$, —NH($C_{1-3}$ alkyl) or —N($C_{1-3}$ alkyl)($C_{1-3}$ alkyl), in particular —OH. In this embodiment, it is further preferred that $R^6$ is in para position in respect of the ring nitrogen atom $N^+$.

Preferred examples of the compound of formula 4 are the compounds 2b, 2c or 2d shown below or pharmaceutically acceptable salts, solvates or prodrugs thereof:

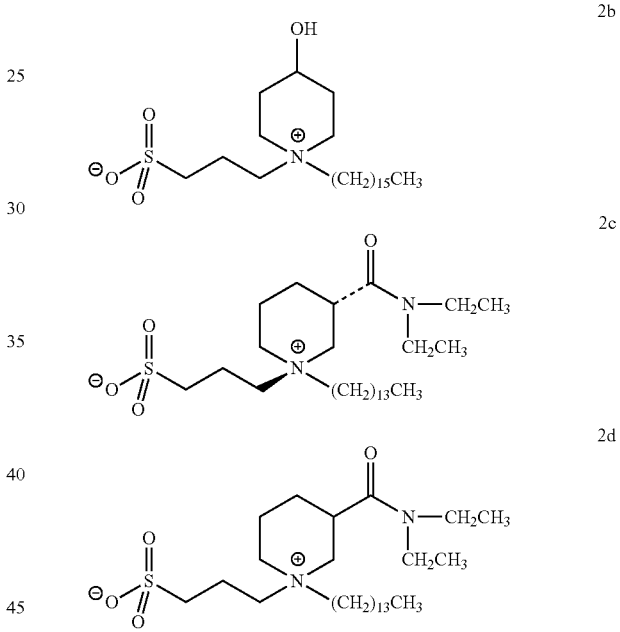

The present invention also relates to a pharmaceutical composition comprising a compound of formula 3 or 4, as described and defined herein, or a pharmaceutically acceptable salt, solvate or prodrug thereof, and a pharmaceutically acceptable excipient.

The invention further relates to a compound of formula 3 or 4, as described and defined herein, or a pharmaceutically acceptable salt, solvate or prodrug thereof, or a pharmaceutical composition comprising any of the aforementioned entities and a pharmaceutically acceptable excipient, for use in the treatment, prevention or amelioration of an inflammatory, autoimmune and/or allergic disorder.

Moreover, the present invention relates to a method of treating, preventing or ameliorating a disease or disorder, in particular an inflammatory, autoimmune and/or allergic disorder, the method comprising the administration of a compound of formula 3 or 4, as described and defined herein, or a pharmaceutically acceptable salt, solvate or prodrug thereof, or a pharmaceutical composition comprising any of the aforementioned entities and a pharmaceutically acceptable excipient, to a subject preferably, a human or a non-human mammal) in need of such a treatment, prevention or amelioration.

The inflammatory, autoimmune and/or allergic disorder to be treated, prevented or ameliorated using the compounds of formula 3 or 4 according to the invention is, for example, selected from: psoriasis, atopic dermatitis (atopic eczema), contact dermatitis, xerotic eczema, seborrheic dermatitis, neurodermitis, dyshidrosis, discoid eczema, venous eczema, dermatitis herpetiformis (Duhring's Disease), autoeczematization, dermatomyasitis, hyper-IgE (Buckley) syndrome, Wiskott-Aldrich syndrome, anaphylaxis, food allergy, or allergic reactions to venomous slings; acute urticarias, chronic urticarias, physical urticarias including aquagenic urticaria, cholinergic urticaria, cold urticaria (chronic cold urticaria), delayed pressure urticaria, dermatographic urticaria, heat urticaria, solar urticaria, vibration urticaria, adrenergic urticaria, or urticaria angioedema; inflammatory bowel disease, Crohn's disease, ulcerative colitis, collagenous colitis, lymphocytic colitis, diversion colitis (diverticulitis), Behcet's syndrome, indeterminate colitis, celiac disease, irritable bowel syndrome, post-operative ileus, eosinophilic gastroenteropathy, or gastritis; chronic allergic rhinitis, seasonal allergic rhinitis (hay-fever), allergic conjunctivitis, chemical conjunctivitis, neonatal conjunctivitis, Sjögren syndrome, open-angle glaucoma, dry eye disease (DED; including, e.g., aqueous tear-deficient dry eye (ADDE). Sjögren syndrome dry eye (SSDE), non-SSDE, or evaporative dry eye (EDE)), or diabetic macular edema (or diabetic retinopathy); chronic obstructive pulmonary disease (COPD), allergic asthma, allergic bronchopulmonary aspergillosis, hypersensitivity pneumonitis, or lung fibrosis; rheumatoid arthritis, juvenile rheumatoid arthritis, ankylosing spondylitis, systemic lupus erythematosus (SLE), scleroderma, osteoarthritis, reactive arthritis, or polymyalgia rheumatica; multiple sclerosis, Guillain-Barre syndrome, Hashimoto's thyroiditis, Grave's disease, temporal arteritis, primary biliary cirrhosis, sclerosing cholangitis, autoimmune hepatitis, alopecia areata or autoimmune lymphoproliferative syndrome (ALPS); a graft-versus-host disease, a host-versus-graft disease or a transplant rejection; or an inflammatory contribution to Alzheimer's disease or Parkinson's disease.

The present invention further provides novel compounds. These compounds are described herein and are characterized by formula 5 or 6 as defined below. The compounds of formula 5 or 6 as provided in the context of the present invention are particularly useful in a medical setting, i.e. as pharmaceuticals. As is evident form the disclosure of the invention, these compounds are particularly useful in the treatment, prevention or amelioration of an inflammatory, autoimmune and/or allergic disorder. The invention thus further provides a method of treating, preventing or ameliorating a disease or disorder, in particular an inflammatory, autoimmune and/or allergic disorder, the method comprising the administration of a compound of formula 5 or 6 as defined below or a pharmaceutical acceptable salt, solvate or prodrug thereof, or a pharmaceutical composition comprising any of the aforementioned entities and a pharmaceutical acceptable excipient, to a subject (preferably, a human or a non-human mammal) in need of such a treatment, prevention or amelioration.

Accordingly, the invention provides a compound of the following formula 5

$$R^5-R^4-X\begin{matrix}R^3\\|\\\diagdown R^2\\R^1\end{matrix}$$

or a pharmaceutical acceptable salt, solvate or prodrug thereof, wherein $R^1$, $R^2$, $R^3$, and X have the meanings or the preferred meanings defined herein above for the compound of formula 3.

$R^4$ in formula 5 is a $C_{1-6}$ alkylene group. The alkylene group may be linear or branched; preferably, the alkylene group is linear. The alkylene group has 1 to 6 (i.e., 1, 2, 3, 4, 5 or 6) carbon atoms and preferably has 2 or 3 carbon atoms, more preferably 3 carbon atoms. It is particularly preferred that $R^4$ is $-(CH_2)_3-$.

If $R^4$ is an alkylene group having 1, 2, 4, 5 or 6 carbon atoms, then $R^5$ is $-SO_3^-$, $-SO_3H$, $-PO_3H-PO_3^{2-}$, $-PO_3H_2$, $-PO_2(OC_{1-3}$ alkyl$)^-$, $-PO_2H(OC_{1-3}$ alkyl$)$, $-PO(OC_{1-3}$ alkyl$)^-$, $-CO_2$, $-CO_2H$, or $-CO_2(C_{1-3}$ alkyl$)$, and preferably is $R^5$ is $-SO_3^-$, $-SO_3H$, $-PO_3H^-$, $-PO_3^{2-}$, or $-PO_3H_2$. If $R^4$ is an alkylene group having 3 carbon atoms, then $R^5$ is $-CO_2$, $-CO_2H$, $-CO_2(C_{1-3}$ alkyl$)$, $-PO_2(OC_{1-3}$ alkyl$)^-$, $-PO_2H(OC_{1-3}$ alkyl$)$, or $-PC(OC_{1-3}$ alkyl$)_2$, and preferably $R_5$ is $-CO_2^-$ or $-CO_2H$. Accordingly, in a particularly preferred embodiment $R^5$ is $-SO_3$ or $-SO_3H$ and $R^4$ is a linear or branched alkylene group having 2, 4, 5 or 6 carbon atoms (preferably, $R^4$ is a linear alkylene group having 2, 4, 5 or 6 carbon atoms). In a further particularly preferred embodiment $R^5$ is $-PO_3^{2-}$, $-PO_3H^-$, or $-PO_3H_2$ and $R^4$ is a linear or branched alkylene group having 2, 4, 5 or 6 carbon atoms (preferably, $R^4$ is a linear alkylene group having 2, 4, 5 or 6 carbon atoms). In a further particularly preferred embodiment, $R^4$ is an alkylene group having 1, 2, 4, 5 or 6 carbon atoms, and $R^5$ is $-PO_3H^-$, $-PO_3^{2-}$, $-PO_3H_2$, $-PO_2(OC_{1-3}$ alkyl$)^-$, $-PO_2H(OC_{1-3}$ alkyl$)$, $-PO_2(OC_{1-3}$ alkyl$)_2$, $-CO_2$, $-CO_2H$, or $-CO_2(C_{1-3}$ alkyl$)$; or $R^4$ is an alkylene group having 3 carbon atoms, and $R^5$ is $-CO_2^-$, $-CO_2H$, $-CO_2(C_{1-3}$ alkyl$)$, $-PO_2(OC_{1-3}$ alkyl$)^{31}$, $-PO_2H(OC_{1-3}$ alkyl$)$, or $-PO(OC_{1-3}$ alkyl$)_2$. Preferred examples of the compound of formula 5 are the compounds 1n, 1q, 1s, 1w or 1x shown below or pharmaceutically acceptable salts, solvates or prodrugs thereof:

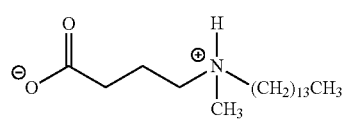

1n

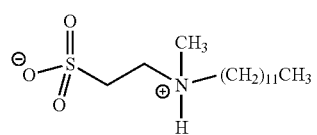

1q

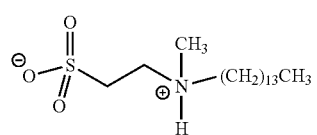

1s

-continued

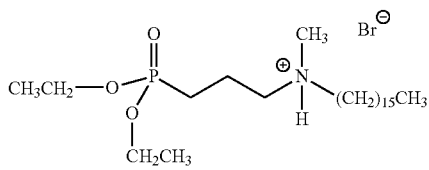

1w

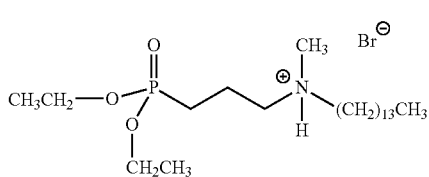

1x

Furthermore, the compound of formula 5 may be a compound of the following formula 6

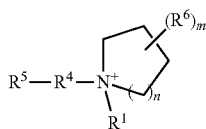

6 or a pharmaceutical acceptable salt, solvate or prodrug thereof, wherein $R^1$, $R^4$ and $R^5$ have the meanings or the preferred meanings defined herein above for the compound of formula 5, and $R^6$, n and m have the meanings or the preferred meanings defined herein above for the compound of formula 4.

The compounds to be used in accordance with the present invention, in particular the compounds of formula 1, 2, 3, 4, 5 or 6, can be prepared by methods known in the field of synthetic chemistry.

For example, compounds of the general formula 1 can be prepared by nucleophilic ring opening of alkanesultones with N-alkylated alkylamines. Alternatively, compounds of the general formula 1 can be prepared by N-alkylation of N-alkylated alkylamines (or other N-alkylated hydrocarbylamines, such as, e.g., N-alkylated alkenylamines or N-alkylated alkynylamines) using ω-chloro- or ω-bromo-1-alkanesulfonates under basic conditions. In a similar way, the related phosphonates or carboxylates are generated, e.g., by using ω-chloro- or ω-bromo-1-alkanephosphonates or ω-chloro- or (ω-bromo-1-alkanecarboxyfates. The corresponding N,N-dialkylated quarternary ammonium derivatives can be obtained by standard N-alkylation using, e.g., alkyl iodides. Compounds of formula 3 or 5 can be prepared as described herein for the compounds of formula 1.

Compounds of the general formula 2 (and, likewise, compounds of formula 4 or 6) can be prepared by consecutive N-alkylation of appropriately functionalised pyrrolidine, piperidine or azepane derivatives using the aforementioned ω-chloro-1-alkanesulfonates, -phosphonates or -carboxylates followed by alkyl iodides.

The compounds of formula 1, 2, 3, 4, 5 or 6 can also be prepared in analogy to the synthetic routes described in the examples section.

As used herein, the term "hydrocarbon group" refers to a group consisting of carbon atoms and hydrogen atoms, which group may be saturated or unsaturated, linear, branched or cyclic, aliphatic or aromatic. A "$C_{10-20}$ hydrocarbon group" denotes a hydrocarbon group having 10 to 20 carbon atoms.

As used herein, the term "alkyl group" refers to a monovalent saturated aliphatic (i.e. non-aromatic) acyclic hydrocarbon group which may be linear or branched and does not comprise any carbon-to-carbon double bond or any carbon-to-carbon triple bond.

As used herein, the term "alkenyl group" refers to a monovalent unsaturated aliphatic acyclic hydrocarbon group which may be linear or branched and comprises at least one carbon-to-carbon double bond while it does not comprise any carbon-to-carbon triple bond.

As used herein, the term "alkynyl group" refers to a monovalent unsaturated aliphatic acyclic hydrocarbon group which may be linear or branched and comprises at least one carbon-to-carbon triple bond and optionally one or more carbon-to-carbon double bonds.

As used herein, the term "alkylene group" refers to a divalent saturated aliphatic (i.e. non-aromatic) acyclic hydrocarbon group which may be linear or branched and does not comprise any carbon-to-carbon double bond or any carbon-to-carbon triple bond.

The scope of the invention embraces all pharmaceutical acceptable salt forms of the compounds of formula 1, 2, 3, 4, 5 or 6, which may be formed, e.g., by protonation of an atom carrying an electron lone pair which is susceptible to protonation, such as an amino group, with an inorganic or organic acid, or as a salt of a carboxylic acid group with a physiologically acceptable cation as they are well-known in the art. Exemplary base addition salts comprise, for example, alkali metal salts such as sodium or potassium salts; alkaline earth metal salts, such as calcium or magnesium salts; ammonium salts; aliphatic amine salts, such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts, such as pyridine salts, picofine salts, quinoline salts or isoquinoline salts; quaternary ammonium salts, such as tetramethylammonium salts, tetraethylammonium salts, benzyltrimethylammnonium salts, benzyltriethylammonium salts, benzyltributylammonium salts, methyltrioctylammonium salts or tetrabutylammonium salts; and basic amino acid salts, such as arginine salts or lysine salts. Exemplary acid addition salts comprise, for example, mineral acid salts, such as hydrochloride, hydrobromide, hydroiodide, sulfate salts, nitrate salts, phosphate salts (such as phosphate, hydrogenphosphate or dihydrogenphosphate salts), carbonate salts, hydrogen carbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts, such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts, such as aspartate or glutamate salts.

Moreover, the scope of the invention embraces solid forms of the compounds of formula 1, 2, 3, 4, 5 or 6 in any solvated form, including e.g. solvates with water, for example hydrates, or with organic solvents such as, e.g., methanol, ethanol, isopropanol or acetonitrile, i.e. as a methanolate, ethanolate, isopropanolate or acetonitrilate, respectively; or in the form of any polymorph.

Furthermore, the formulae in the present application are intended to cover all possible stereoisomers, including enantiomers and diastereomers, of the indicated compounds.

Thus, all stereoisomers of the compounds of the present invention, in particular the compounds of formula 1, 2, 3, 4, 5 or 6, are contemplated as part of the present invention, either in admixture or in pure or substantially pure form. The scope of the compounds according to the invention embraces all the possible stereoisomers and their mixtures. It very particularly embraces the racemic forms and the isolated optical isomers. The racemic forms can be resolved by physical methods, such as, e.g., fractional crystallization, separation or crystallization of diastereomeric derivatives or separation by chlral column chromatography. The individual optical isomers can be obtained from the racemates using conventional methods, such as, e.g., salt formation with an optically active acid followed by crystallization.

Pharmaceutically acceptable prodrugs of compounds of the present invention, in particular of the compounds of formula 1, 2, 3, 4, 5 or 6, are derivatives which have chemically or metabolically cleavable groups and become, by solvolysis or under physiological conditions, the compounds of the present invention which are pharmaceutical active in vivo. Prodrugs of compounds of the present invention may be formed in a conventional manner with a functional group of the compounds such as with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Prodrugs include acid derivatives well known to the person skilled in the art, such as, for example, esters prepared by reaction of the parent acidic compound with a suitable alcohol, or amides prepared by reaction of the parent acid compound with a suitable amine. When a compound of the present invention has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester, N,N-diethylglycolamidoester or α-acetoxyethylester. When a compound of the present invention has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(=O)—CH$_3$, —OC(=O)—C$_2$H$_5$, —OC(=O)-(tert-Bu), —OC(=O)..C$_{15}$H$_{31}$, —OC(=O)-(m-COONa-Ph), —OC(=O)—CH$_2$CH$_2$COONa, —O(C=O)—CH(NH$_2$)CH$_3$ or —OC(=O)—CH$_2$—N(CH$_3$)$_2$. When a compound of the present invention has an amino group, an amide derivative prepared by reacting the amino group with a suitable acid halide or a suitable mixed anhydride is exemplified as a prodrug. An especially preferred amide derivative as a prodrug is —NHC(=O)—(CH$_2$)OCH$_3$ or —NHC(=O)—CH(NH$_2$)CH$_3$.

The compounds described herein may be administered as compounds per se in their use as pharmacophores or pharmaceutical compositions or may be formulated as medicaments. Within the scope of the present invention are pharmaceutical compositions comprising as an active ingredient a compound of formula 1, 2, 3, 4, 5 or 6 as defined above. The pharmaceutical compositions may optionally comprise one or more pharmaceutical acceptable excipients, such as carriers, diluents, fillers, disintegrants, lubricating agents, binders, colorants, pigments, stabilizers, preservatives, or antioxidants.

The pharmaceutical compositions can be formulated by techniques known to the person skilled in the art, such as the techniques published in Remington's Pharmaceutical Sciences, 20th Edition. The pharmaceutical compositions can be formulated as dosage forms for oral, parenteral, such as intramuscular, intravenous, subcutaneous, intradermal, intraarterial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds according to the invention, in particular the compounds of formula 1, 2, 3, 4, 5 or 6, or the above described pharmaceutical compositions comprising one or more compounds of formula 1, 2, 3, 4, 5 or 6 may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e.g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g. through mouth or nose), gastrointestinal, intrauterine, intraocular, subcutaneous, ophthalmic (including intravitreal or intracameral), rectal, and vaginal.

If said compounds or pharmaceutical compositions are administered parenterally, then examples of such administration include one or more of: intravenously, intraarterially, intraperitoneally, intrathecally, intraventricular, intraurethrally, intrastemally, intracranially, intramuscularly or subcutaneously administering the compounds pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients, such as microcrystalline cellulose, lactose, sodium citrate, calcium carbonate, dibasic calcium phosphate and glycine, disintegrants, such as starch (preferably corn, potato or tapioca starch), sodium starch glycolate, croscarmellose sodium and certain complex silicates, and granulation binders, such as polyvinylpyrrolidone, hydroxypropylmethylcellulose (HPMC), hydroxypropylcellulose (HPC), sucrose, gelatin and acacia. Additionally, lubricating agents, such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents, such as water, ethanol, propylene glycol and glycerin, and combinations thereof.

Alternatively, said compounds or pharmaceutical compositions can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

Said compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative, such as a benzylalkonium chloride. Alternatively, they may be formulated in an ointment, such as petrolatum.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds of formula 1, 2, 3, 4, 5 or 6 for administration to a human (of approximately 70 kg body weight) may be 0.05 to 5000 mg, preferably 0.1 mg to 1000 mg, of the active ingredient per unit dose. The unit dose may be administered, for example, 1 to 4 times per day. The dose will depend on the route of administration. It will be appreciated that it may be necessary to make routine variations to the dosage depending on the age and weight of the patient/subject as well as the severity of the condition to be treated. The precise dose and route of administration will ultimately be at the discretion of the attendant physician or veterinarian.

The compounds of the present invention, including the compounds of formula 1, 2, 3, 4, 5 or 6, may be administered in the context of a monotherapy or in cotherapy with one or more other pharmaceutical agents. For example, one compound of the present invention or two or more compounds of the invention may be used in combination with one or more immunomodulatory drugs and/or anti-inflammatory drugs for the treatment, prevention or amelioration of an inflammatory, autoimmune and/or allergic disorder.

A pharmaceutical composition may comprise said compound(s), immunomodulatory drug(s) and/or anti-inflammatory drug(s). Cotherapy may also include the administration of two or more compounds of the present invention in the absence of further immunomodulatory drugs or anti-inflammatory drugs. It is also envisaged herein that the compound(s), immunomodulatory drug(s) and/or anti-inflammatory drug(s) might be linked, for example, by formation of conjugates. Accordingly, the compounds, immunomodulatory drugs and/or anti-inflammatory drugs may be administered to a subject simultaneously. Also, a pharmaceutical composition may comprise only the compound(s) of the present invention, while the one or more immunomodulatory drugs and/or anti-inflammatory drugs are comprised in a different pharmaceutical composition. In that case, it may still be possible to administer the compound(s) of the invention, immunomodulatory drugs and/or anti-inflammatory drugs simultaneously; however, the compound(s) of the invention may also be administered before and/or after the one or more immunomodulatory drugs and/or anti-inflammatory drugs. It is readily apparent to a person skilled in the art how to administer, for example, one or more compounds of the present invention, one or more immunomodulatory drugs, and/or one or more anti-inflammatory drugs in cotherapy.

It is envisaged that one or more of the compounds as described herein, in particular the compounds of formula 1, 2, 3, 5 or 6, may be used in combination with one or more immunomodulatory drugs and/or one or more anti-inflammatory drugs.

The one or more immunomodulatory drugs include, without being limited thereto: antimetabolites such as, e.g., azathioprine, mycophenolic acid, leflunomide, teriflunomide, or methotrexate; macrolides such as, e.g., tacrolimus, ciclosporin, or pimecrolimus; IL-2 inhibitors such as, e.g., abetimus or gusperimus; TNF-α inhibitors such as, e.g., thalidomide or lenalidomide; IL-1 receptor antagonists such as, e.g., anakinra; mammalian target of rapamycin (mTOR) proteins such as, e.g., sirolimus, deforolimus, everolimus, temsirolimus, zotarolimus, or blolimus A9; monoclonal antibodies such as, e.g., eculizumab, infliximab, adalimumab, certolizumab pegol, afelimomab, golimumab, Mepolizumab, omalizumab, nerelimomab, faralimomab, elsilimomab, lebrikizumab, ustekinumab, muromonab-CD3, otelixizumab, teplizumab, visilizumab, clenoliximab, keliximab, zanolimumab, efalizumab, erlizumab, afutuzumab, ocrelizumab, pascolizumab, lumilliximab, teneliximab, toralizumab, aselizumab, galiximab, gavilimomab, ruplizumab, belimumab, ipilimumab, tremelimumab, bertilimumab, lerdelimumab, metelimumab, natalizumab, tocilizumab, odulimomab, basiliximab, daclizumab, inolimomab, zolimomab aritox, atorolimumab, cedelizumab, dorlixizumab, fonlolizumab, gantenerumab, gomiliximab, maslimomab, morolimumab, pexelizumab, reslizumab, rovelizumab, siplizumab, talizumab, telimomab aritox, vapaliximab, or vepalimomab; polyclonal antibodies such as, e.g., anti-thymocyte globulin or anti-lymphocyte globulin; or fusion proteins such as, e.g., abatacept, belatacept, etanercept, pegsunercept, aflibercept, alefacept, or rilonacept.

Furthermore, the one or more anti-inflammatory drugs include, without being limited thereto: pyrazolidine or butylpyrazolidine derivatives such as, e.g., ampyrone, clofezone, kebuzone, metamizole, mofebutazone, oxyphenbulazone, phenazone, phenylbutazone, sulfinpyrazone, or feprazone; acetic acid derivatives such as, e.g., aceclofenac, acemetacin, alclofenac, bromfenac, bumadizone, bufexamac, diclofenac, difenpiramide, etodoiac, fentiazac, indometacin, ketorolac, lonazolac, oxametacin, proglumetacin, sulindac, tolmetin, zomepirac, or amfenac; oxicam derivatives such as, e.g., ampiroxicam, droxicam, lornoxicam, meloxicam, piroxicam, or lenoxicam; propionic acid derivatives such as, e.g., alminoprofen, benoxaprofen, dexibuprofen, dexketoprofen, fenbufen, fenoprofen, flunoxaprofen, flurbiprofen, ibuprofen, ibuproxam, indoprofen, ketoprofen, naproxen, oxaprozin, pirprofen, suprofen, or tiaprofenic acid; fenamic acid derivatives such as, e.g., flufenamic acid, meclofenamic acid, mefenamic acid, tolfenamic acid, niflumic acid, morniflumate, or azapropazone; COX-2 inhibitors such as, e.g., celecoxib, etoricoxib, iumiracoxib, parecoxib, rofecoxib, or valdecoxib; or nabumetone, glucosamine, benzydamine, glycosaminoglycan, magnesium salicylate, proquazone, superoxide dismutase/orgotein, nimesulide, diacerein, tenidap, oxaceprol, or chondroitin sulfate.

Cotherapy using the compound(s) of the present invention, immunomodulatory drug(s) and/or anti-inflammatory drug(s) may result in a synergistic effect, i.e. the agents acting together may create an effect greater than that predicted by knowing only the separate effects of the individual agents. Such a synergistic effect might be particularly advantageous if less amounts of the compound (s), immunomodulatory drug(s) and/or anti-inflammatory drug(s) may then be used. Thus, possible side-effects of the compound(s), immunomodulatory drug(s) and/or anti-inflammatory drug(s) might be diminished or avoided.

It is furthermore particularly envisaged that one or more of the compounds of the invention, in particular the compounds of formula 1, 2, 3, 4, 5 or 6, may be used in combination with one or more immunomodulatory drugs as described herein above and/or one or more anti-inflammatory drugs as described herein above (including, for example, azathioprine, ciclosporin, D-penicillamine, gold salts, hydroxychloroquine, leftunomide, methotrexate, minocycline, sulfasalazine, or cyclophosphamide) for the treatment, prevention or amelioration of rheumatoid arthritis.

The term "treatment of a disorder or disease" as used herein, such as "treatment of an inflammatory, autoimmune and/or allergic disorder", is well known in the art. "Treatment of a disorder or disease" implies that a disorder or disease is suspected or has been diagnosed in a patienty-subject. A patient/subject suspected of suffering from a disorder or disease typically shows specific clinical and/or pathological symptoms which a skilled person can easily attribute to a specific pathological condition (i.e., diagnose a disorder or disease).

"Treatment of a disorder or disease" may, for example, lead to a halt in the progression of the disorder or disease (e.g., no deterioration of symptoms) or a delay in the progression of the disorder or disease (in case the halt in progression is of a transient nature only). "Treatment of a disorder or disease" may also lead to a partial response (e.g., amelioration of symptoms) or complete response (e.g., disappearance of symptoms) of the subject/patient suffering from the disorder or disease. "Amelioration" of a disorder or disease may, for example, lead to a halt in the progression of the disorder or disease or a delay in the progression of the disorder or disease. Such a partial or complete response may be followed by a relapse. It is to be understood that a subject/patient may experience a broad range of responses to a treatment (e.g., the exemplary responses as described herein above).

Treatment of a disorder or disease may, inter alia, comprise curative treatment (preferably leading to a complete response and eventually to heating of the disorder or disease) and palliative treatment (including symptomatic relief).

Also the term "prevention of a disorder or disease" as used herein, such as "prevention of an inflammatory, autoimmune and/or allergic disorder", is well known in the art. For example, a patient/subject suspected of being prone to suffer from a disorder or disease as defined herein may, in particular, benefit from a prevention of the disorder or disease. The subject/patient may have a susceptibility or predisposition for a disorder or disease, including but not limited to hereditary predisposition. Such a predisposition can be determined by standard assays, using, for example, genetic markers or phenotypic indicators, it is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of compounds of the present invention before any clinical and/or pathological symptoms are diagnosed or determined or can be diagnosed or determined by the attending physician.

The subject or patient, such as the subject in need of treatment, prevention or amelioration, may be a eukaryote, an animal, a vertebrate animal, a mammal, a rodent (e.g. a guinea pig, a hamster, a rat, a mouse), a murine (e.g. a mouse), a canine (e.g. a dog), a feline (e.g. a cat), an equine (e.g. a horse), a primate, a simian (e.g. a monkey or ape), a monkey (e.g. a marmoset, a baboon), an ape (e.g. gorilla, chimpanzee, orangutan, gibbon), or a human. The meaning of the terms "eukaryote", "animal", "mammal", etc. is well known in the art and can, for example, be deduced from Wehner und Gehring (1995; Thieme Verlag). In the context of this invention, it is particularly envisaged that animals are to be treated which are economically, agronomically or scientifically important. Scientifically important organisms include, but are not limited to, mice, rats, rabbits, fruit flies like Drosophila melagonaster and nematodes like *Caenorhabditis elegans*. Non-limiting examples of agronomically important animals are sheep, cattle and pig, while, for example, cats and dogs may be considered as economically important animals. Preferably, the subject/patient is a mammal; more preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orangutan, a gibbon, a sheep, cattle, or a pig; and in particular a canine, such as a dog); even more preferably, the subject/patient is a human. In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Figure 1B:
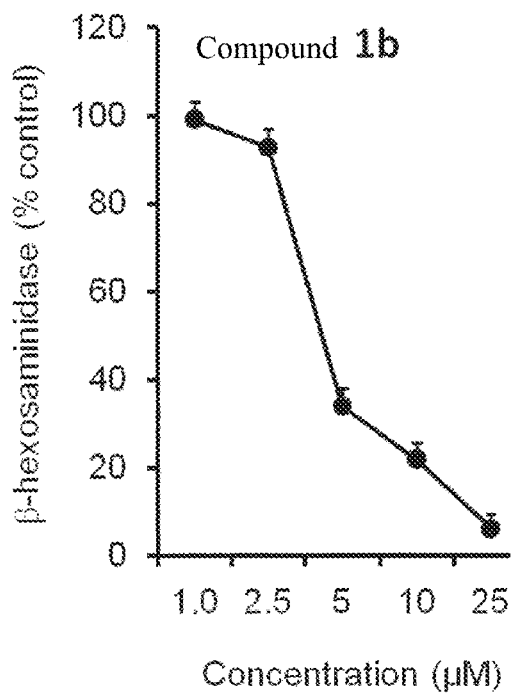
Figure 1C:
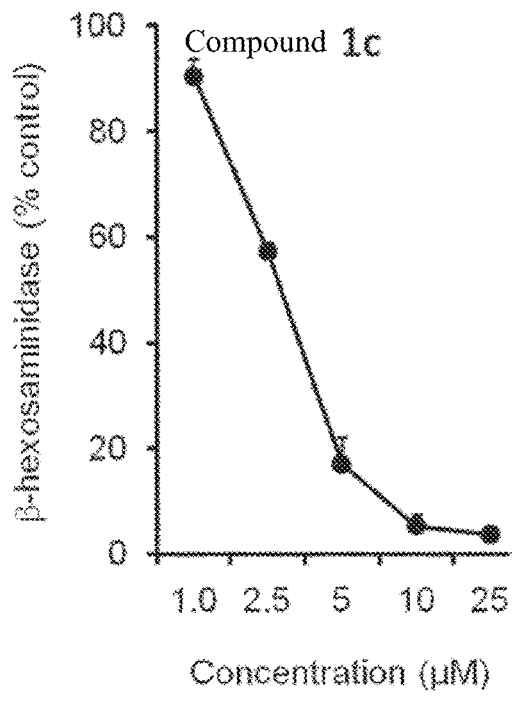
Figure 1D:
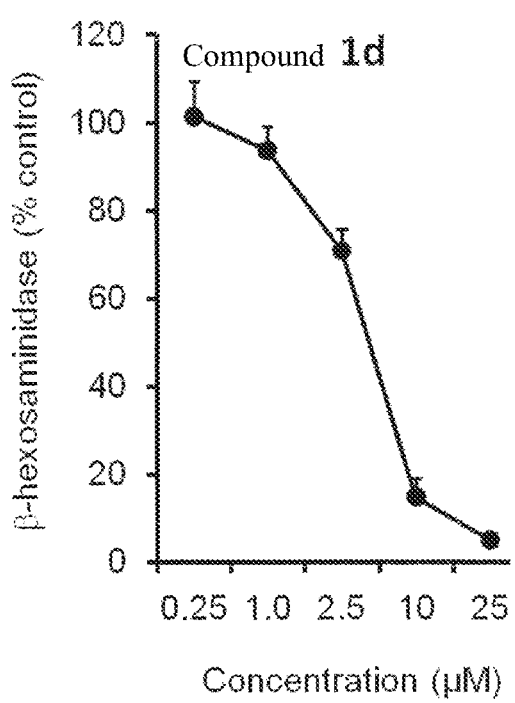
Figure 1I:
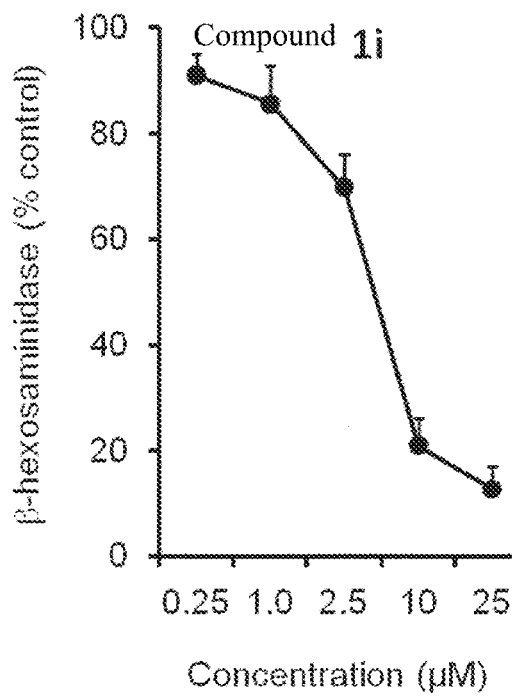
Figure 1J:
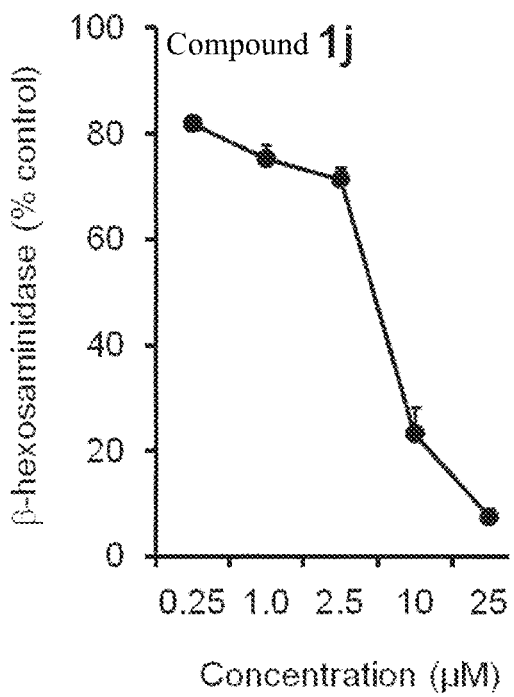
Figure 1K:
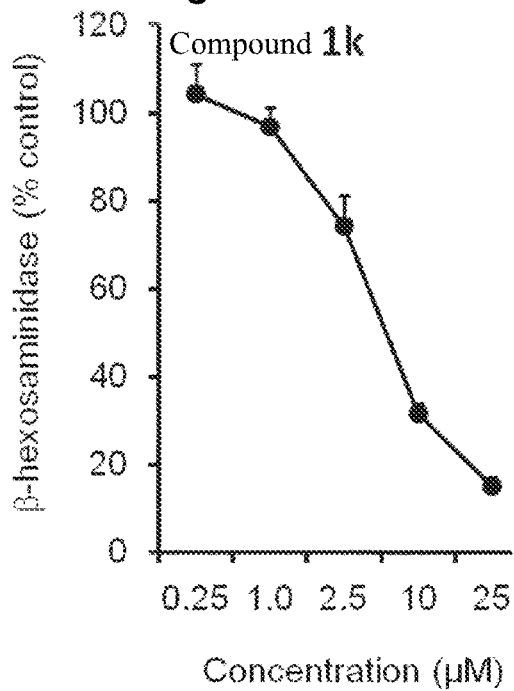
Figure 1L:
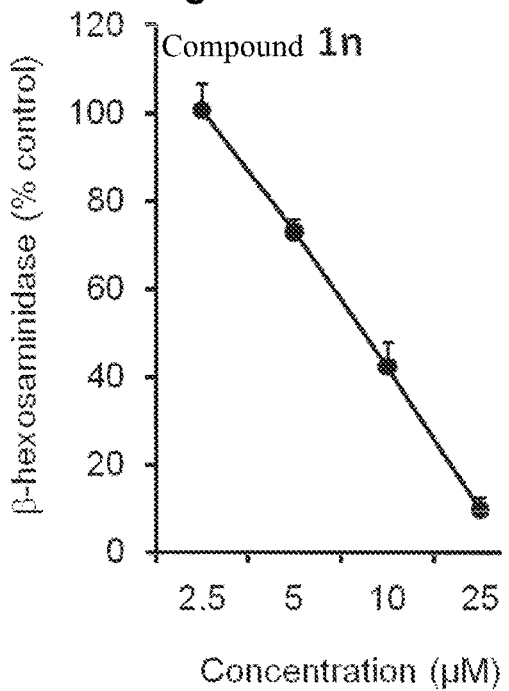
Figure 1M:
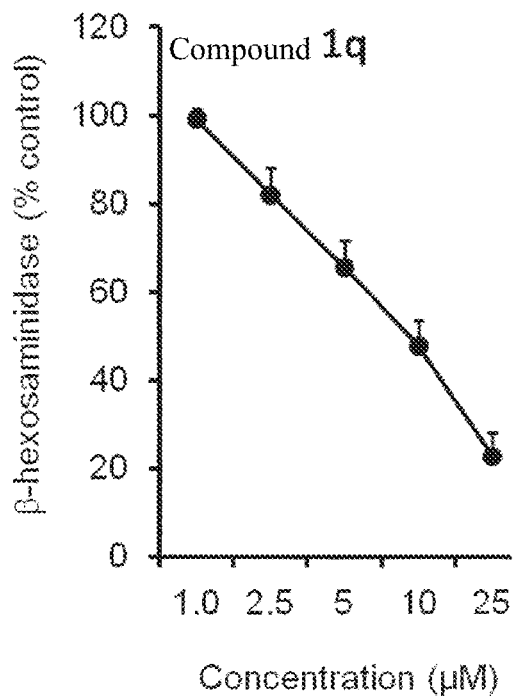
Figure 1N:
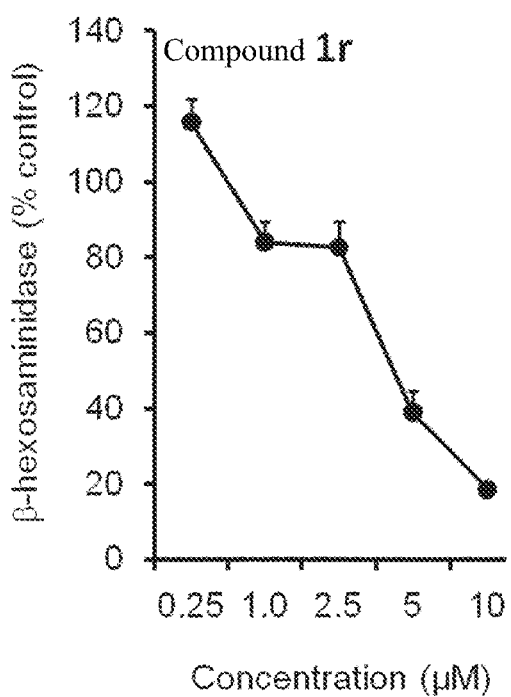
Figure 1O:
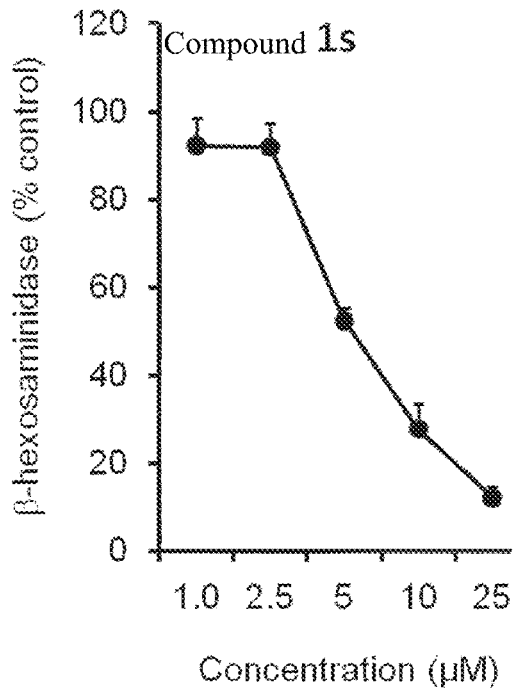
Figure 1P:
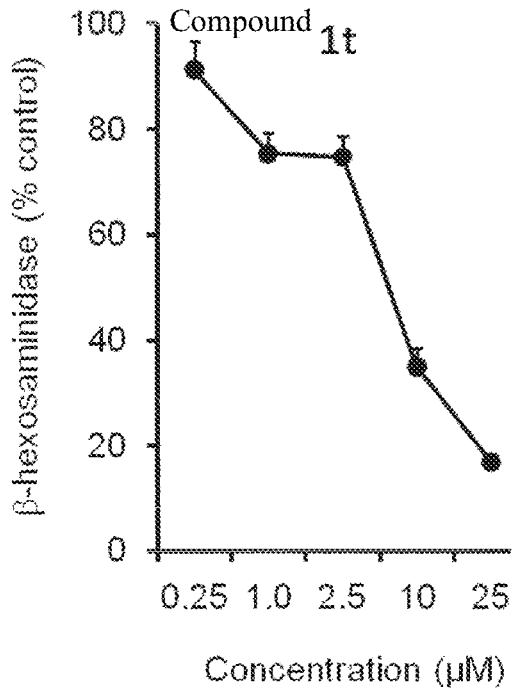
Figure 1Q:
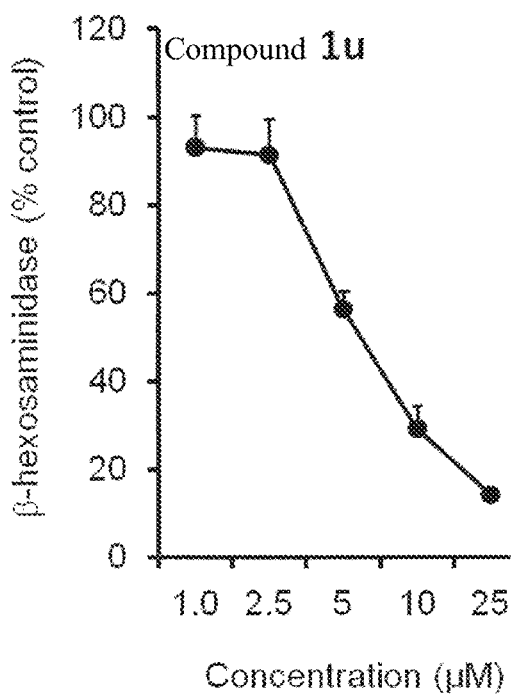
Figure 1R:
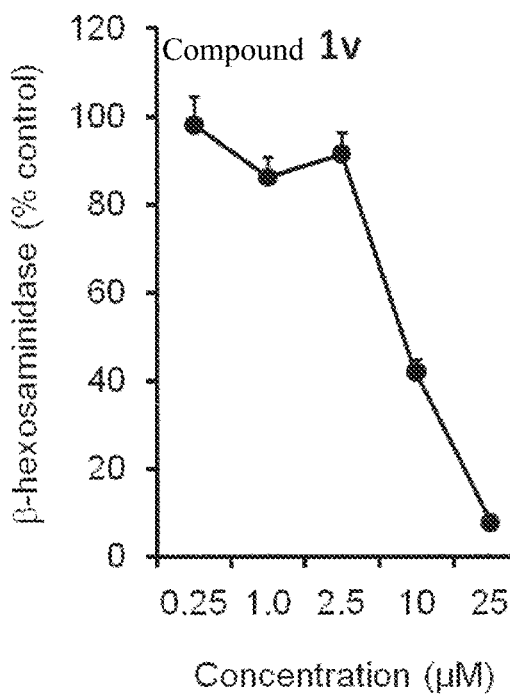
Figure 1S:
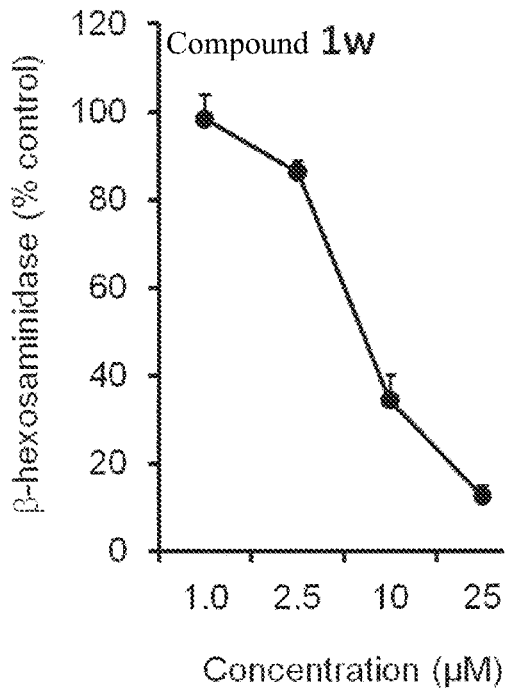
Figure 1T:
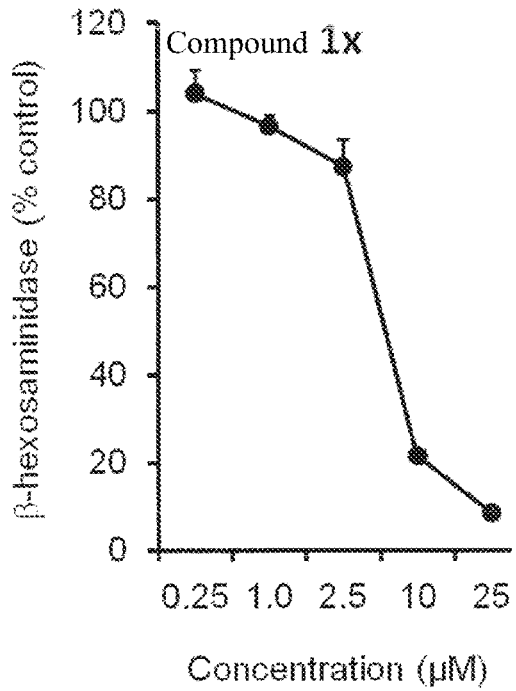
Figure 1U:
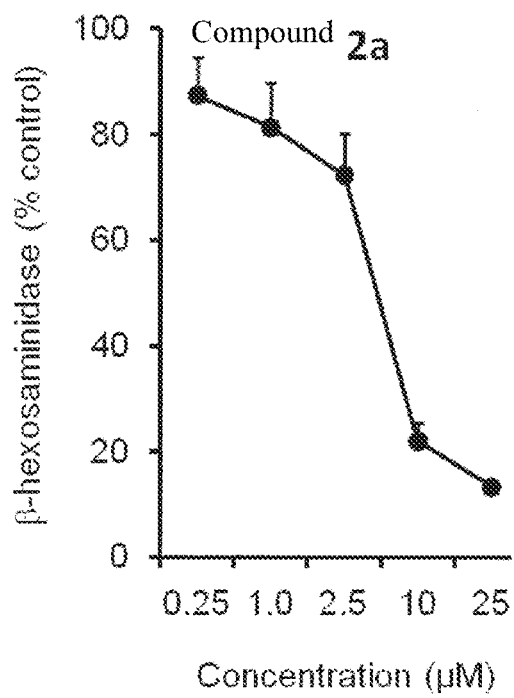
Figure 1V:
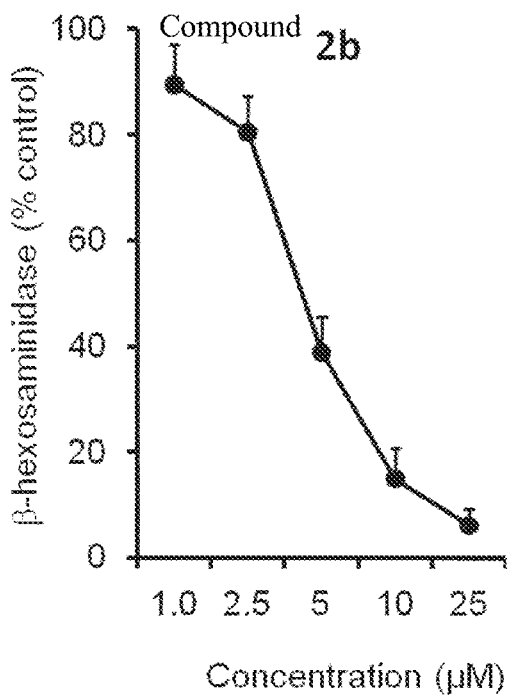
Figure 1W:
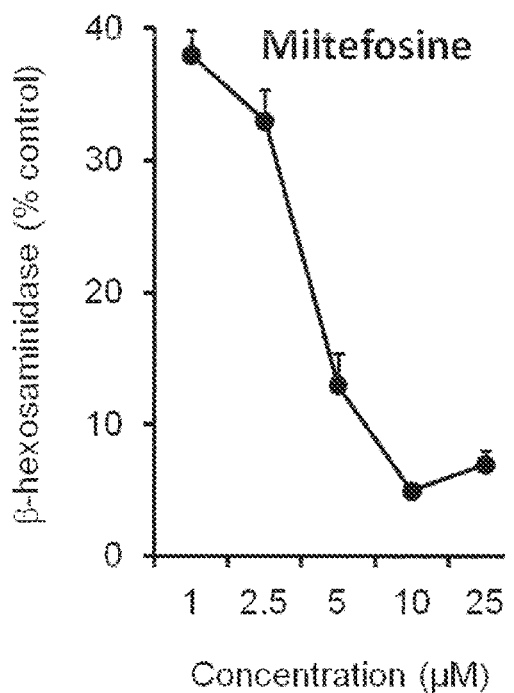

The invention is also described by the following illustrative figures. The appended figures show:

FIGS. 1A-1W: Inhibition of mast cell degranulation by compounds 1a (FIG. 1A), 1b (FIG. 1B), 1c (FIG. 1C), 1d (FIG. ID), 1e (FIG. 1E), 1f (FIG. 1F), 1g (FIG. 1G), 1h (FIG. 1H), 1i (FIG. 1I), 1j (FIG. 1J), 1k (FIG. IK), 1n (FIG. 1L), 1q (FIG. 1M), 1r (FIG. 1N), 1s (FIG. 1O), 1t (FIG. 1P), 1u (FIG. 1Q), 1v (FIG. 1R), 1w (FIG. 1S), 1x (FIG. IT), 2a (FIG. 1U), 2b (FIG. 1V) and miltefosine (FIG. 1W). Dose-response curves for inhibition of β-hexosaminidase release from RBL-2H3 cells stimulated with antigen-specific lgE and triggered with antigen are shown (means±standard error of the mean).

Figure 2A:
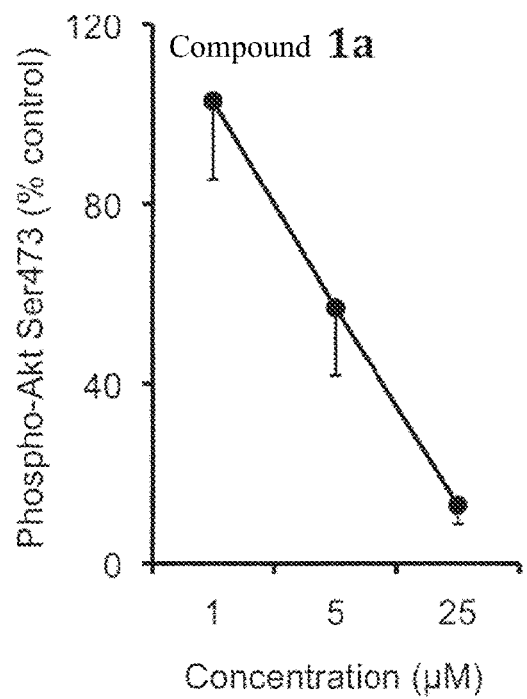
Figure 2B:
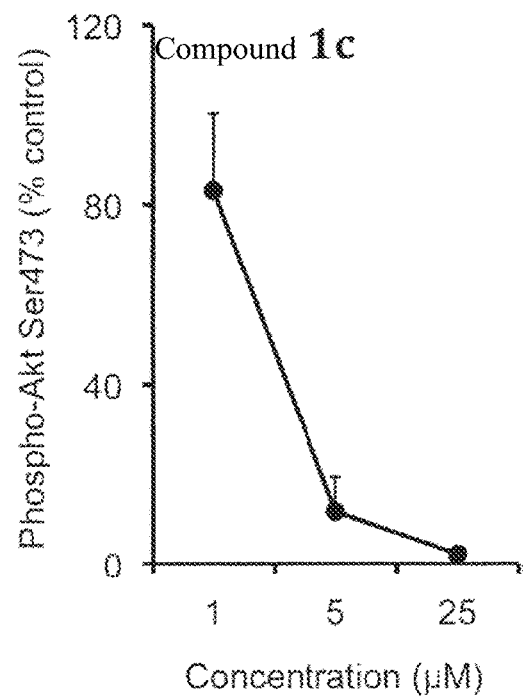

FIGS. 2A & 2B: Inhibition of Akt phosphorylation on Ser473 by compounds 1a (FIG. 2A) and 1c (FIG. 2B). Percentage of total Akt phosphorylated on Ser473 is expressed as a percentage of control untreated cells induced with IgE and antigen for 15 min (shown are means±standard deviation).

Figure 3:
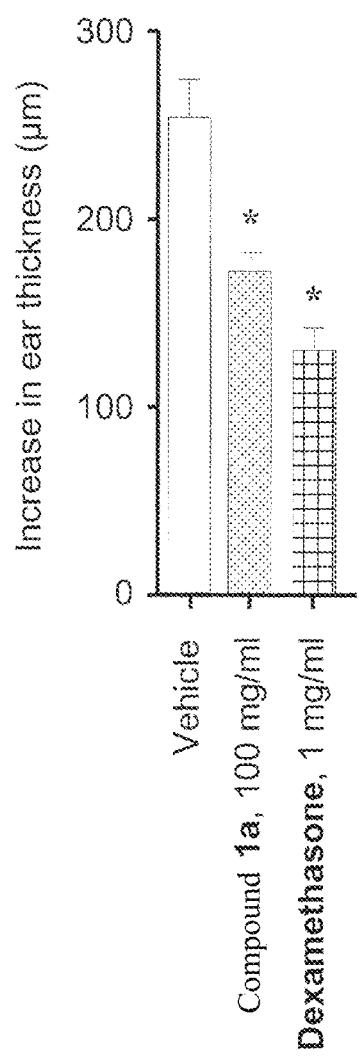

FIG. 3: Effect of compound 1a and dexamethasone on mouse ear swelling in the DTH response in mice (data are means±standard deviations of 8 mice; * $p<0.01$ vs. vehicle control (Dunnett's post hoc test)).

Figure 4A:
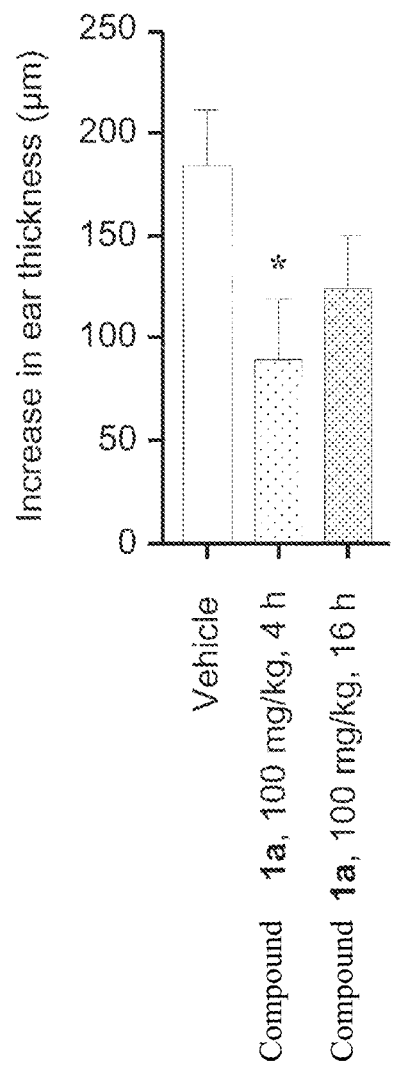
Figure 4B:
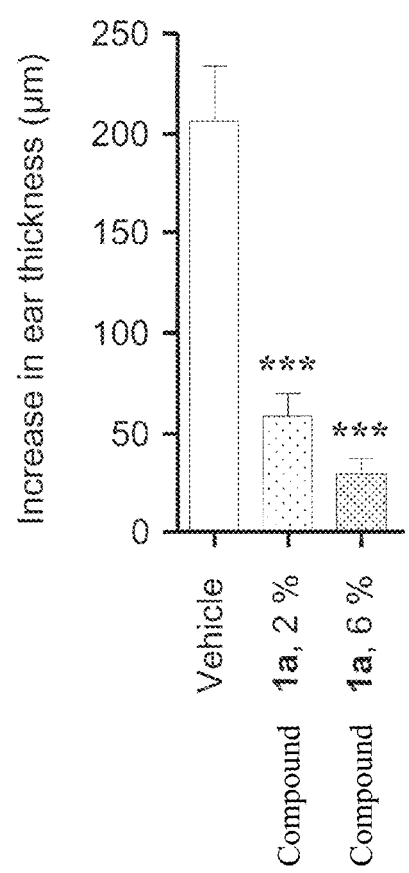

FIGS. 4A & 4B: Effect of compound 1a on mouse ear swelling in the allergic contact dermatitis model in mice. FIG. 4A shows the inhibitory activity of compound 1a at different administration times before antigen challenge (data are means±SEM of 7 mice; * $p<0.05$ vs. vehicle control (Dunnett's post hoc test)). FIG. 4B shows the inhibitory activity of compound 1a after topical application (data are means±SEM of 7 mice; *** $p<0.001$ vs. vehicle control (Dunnett's post hoc test)).

The invention will now be described by reference to the following examples which are merely illustrative and are not to be construed as a limitation of the scope of the present invention.

EXAMPLES

Example 1:
3-(N,N-Dimethylmyristylammonio)-Propanesulfonate 1a

Compound 1a is commercially available (Sigma-Aldrich Chemie GmbH, Munich, Germany, product number T7763).

Example 2: Preparation of
3-(N-Methyltetracylammonio)Propanesulfonate 1b

N-Methyltetradecylamine (454 mg, 2 mmol) and 1,3-propanesultone (280 mg, 2.3 mmol) are stirred in ethyl acetate (10 mL) for 24 h. The volatiles are removed and the residue is flash-chromatographed on silica using dichloromethane/methanol (4:1). Rotary evaporation and drying in high vacuum yields 363 mg (52%) of 1b as a white solid.

$^1$H-NMR (300 MHz, CDCl$_3$) δ=0.81 (t. J-6.9, 3 H), 1.1-1.35 (m, 22H), 1.25 (m, 2H), 2.22 (m, 2H), 2.81 (s, 3H), 2.98 (m, 4H), 3.25 (m, 2H).

MS (ESI): 350.3 (M+H$^+$), 372.6 (M+Na$^+$), 699.6 (2M+H$^+$), 721.6 (2M+Na$^+$).

Example 3: Preparation of
3-N,N-Dimethylmyristylammoniopropylphosphonic Acid 1c

N,N-Dimethyltetradecylamine is alkylated with commercial diethyl 3-bromopropyl-phosphonate to yield the corresponding ethyl ester, which is purified by crystallization. Treatment with trimethylsilyibromide in the presence of allyltrimethylsilana (Hammerschmidt 1991, Yan 2007) followed by hydrolysis of the resulting silylphosphonate yields compound 1c as hydrobromide salt (1c-HBr).

The side products of the ester cleavage are volatile and can be removed in vacuum. 1c-HBr is subsequently purified by crystallization. The amount of water used should be kept to a minimum because 1c and its hydrobromide tend to intense foaming during rotary evaporation. Attempted aqueous workup of the abovementioned ethyl ester, 1c-HBr or 1c results in a stable emulsion. The hydrobromide is treated with exactly one equivalent of NaOH, desalted by passing through a RP-18 column and the resulting betaine 1c is purified by recrystallization.

$^1$H-NMR (600 MHz, CDCl$_3$/CD$_3$OD 8:2): δ=0.90 (t, 3H), [1.22-1.43 (m), 1.39 (br s), Σ=22H)], 1.66 (d/t, J=17.3/7.0, 2H), 1.75 (br m, 2H), 2.02 (m, 2H), 3.09 (s, 6H), 3.25 (m, 2H), 3.47 (m, 2H).

Example 4: Preparation of
2-(N,N-Dimethyltetradecylammonio)Ethanesulfonate 1d

Sodium-2-bromoethansulfonate (411 mg, 1.95 mmol), N-methyltetradecylamine (342 mg, 1.50 mmol) and K$_2$CO$_3$ (269 mg, 1.95 mmol) are suspended in dimethylformamide (DMF) (3 mL) and stirred at reflux overnight. The volatiles are removed and the residue is purified by preparative HPLC to give, after drying at high vacuum, 324 mg of 2-(N-methyltetradecylammonio)-ethanesulfonate as a white solid.

2-(N-Methyltetradecylammonio)-ethanesulfonate (113 mg, 0.25 mmol), methyl iodide (284 mg, 2.0 mmol) and K2 CO$_3$ (103 mg, 0.75 mmol) are suspended in a mixture of acetone (3 mL) and dichloromethane (1 mL). The mixture is stirred at room temperature overnight, the solvent is removed and the residue purified by preparative HPLC to give 50 mg (57%) of 1d.

$^1$H-NMR (300 MHz, CDCl$_3$/CD$_3$OD 8:2); δ5=0.80 (t, J=6.9, 3H), 1.1-1.45 (m, 22H), 1.68 (m, 2H), 3.02 (s, 6H), 3.19 (m, 4H), 3.61 (m, 2H).

MS (ESI): 350.3 (M+H$^+$), 699.6 (2M+H$^+$).

Example 5: Preparation of
4-(N1N-Dimethylmyristylammonio)Butanesulfonate 1e 1,4-Butane sultone (681 mg, 5 mmol) and N,N-dimethyltetradecylamin (966 mg, 4 mmol) are dissolved in DMF (10 mL) and stirred under argon atmosphere at 130° C. bath temperature for 2 d. The volatiles are removed and the residue is purified by preparative HPLC to yield 831 mg (55%) of 1e as white solid.

$^1$H-NMR (300 MHz, CDCl$_3$): δ=0.81 (t, J=6.9, 3H), 1.1-1.35 (m, 22H), 1.61 (m, 2H), 1.83 (m, 4H), 2.84 (m, 2H), 3.08 (s, 6H), 3.18 (m, 2H), 3.44 (m, 2H).

MS (ESI): 378.3 (M+H$^+$). 755.6 (2M+H$^+$).

Example 6: Preparation of 2-((Dimethyl(Tetradecyl)Ammonio)Methyl)Butane-1-Sulfonate 1f Ethylmalonic acid diethylester (1.86 g, 9.9 mMol) and N-methyltetradecyl amine (1.5 g, 6.6 mmol) are dissolved in DMF (20 mL) and stirred at 130° C. bath temperature under argon atmosphere for 24 h. The mixture is partitioned between water and EtOAc. The aqueous layer is extracted with EtOAc twice and the combined EtOAc layers are washed with sat. NaCl, dried over Na$_2$SO$_4$ and the solvent is removed. The residue is passed through a short plug of silica using dichloromethane/methanol 4:1, the solvent removed under reduced pressure and the residue is dried in high vacuum to provide 2.1 g (86%) of ethyl 2-(methyl (tetradecyl)carbamoyl)butanoate as a white material.

Under argon atmosphere, LiAlH$_4$, (608 mg, 16.0 mmol) is suspended in 10 mL of tetrahydrofuran (THF) and heated to reflux. A solution of ethyl 2-(methyl(tetradecyl)-carbamoyl) butanoate (3.0 g, 8.0 mmol) in 15 mL of THF is added dropwise with caution and the resulting mixture is heated to reflux overnight. Methanol is added dropwise with caution until the evolution of hydrogen ceases. 15 mL of water are added, whereupon the colour changes from grey to white. The mixture is diluted with water and ethyl acetate. The solids are filtered off using a pad of celite with EtOAc-washing. The aqueous layer is separated and extracted three times with ethyl acetate. The combined organic layers are washed with sat. NaCl (1×), dried over Na$_2$SO$_4$ and the solvent is removed under reduced pressure. The residue is chromatographed on silica using dichloromethane/methanol 10:1 to yield 550 mg (22%) of 2-((methyl(tetradecyl)amino) methyl)butan-1-ol as a white solid.

2-((Methyl(tetradecyl)amino)methyl)butan-1-ol (390 mg, 1.24 mmol) is dissolved in dichloromethane (8 mL) under argon atmosphere. N,N-Diisopropylethylamine (DIEA) (163 mg, 1.30 mmol) and 4-dimethylaminopyridine (DMAP) (15 mg, 0.12 mmol) are added. To this mixture is added dropwise methanesulfonyl chloride (148 mg, 1.30 mmol). The mixture is stirred at ambient temperature overnight. The mixture is quenched with methanol and the solvent is removed under reduced pressure. Chromatography on silica using dichloromethane/methanol 10:1 yields 208 mg (43%) of 2-((methyl(tetradecyl)amino)-methyl)butyl methanesulfonate.

2-((Methyl(tetradecyl)amino)-methyl)butyl methanesulfonate (200 mg, 0.5 mmol) is dissolved in ethanol (2 mL). A solution of Na$_2$SO$_3$ (315 mg, 2.5 mmol) in 1 mL of water is added and the mixture is stirred at 100° C. bath temperature for 3 h. After removal of the solvent under reduced pressure, the residue is chromatographed on silica using dichloromethane/methanol 20:1 to yield 120 mg (64%) of 2-((methyl(tetradecyl)ammonio)methyl)butane-1-sulfonate. 2-((Methyl(tetradecyl)ammonio)methyi)butane-1-sulfonate (90 mg, 0.23 mmol) is dissolved in 2 mL of dichloromethane under argon atmosphere. K$_2$CO$_3$ (97 mg, 0.70 mmol) and methyl iodide (255 mg, 1.80 mmol) are added and the mixture is stirred at room temperature overnight. After removing the solvent under reduced pressure, the residue is purified by preparative HPLC to yield 78 mg (87%) of 1 f as a white solid.

$^1$H-NMR (300 MHz, CDCl$_3$): δ=0.81 (t, J=6.9, 3H), 0.92 (t, J=7.3, 3H), 1.1-1.35 (m, 22H), 1.50 (m, 2H), 1.66 (m, 2H), 2.40 (m, 1H), 2.75 (m, 1H), 2.91 (d/m, J=12.5, 1H). 3.10 (m, 1H), 3.12/3.16 (2s, 3H), 3.26 (m, 2H), 4.06 (d/m, J=12.9, 1H).

MS (ESI): 392.4 (M+H$^+$), 783.7 (2M+H$^+$).

Examples 7, 8 and 9: Preparation of 3-(N,N-Dimethyloctadecylammonio)Propanesulfonate 1g, 3-(N, N-dimethylpalmitylammonio)propansulfonate 1h and 3-(N,N-dimethyldodecyl-ammonio) propanesulfonate 1i Compounds 1g, 1h and 1i are prepared in a similar way as described for compound 1b using N-methyloctadecylamine (for 1g), N-methylhexadecylamine (for 1h) or N-methyldodecyl-amine (for 1i) instead of N-methyltetradecylamine followed by quarternization of the nitrogen using methyl iodide as described in the final preparation step for compound 1d.

Alternatively, compounds 1g, 1h and 1i are commercially available from Sigma-Aldrich GmbH, Munich, Germany (1g: product number 41570; 1h: product number H6883; 1i: product number D0431).

Example 10: N-Tetradecyl-N,N-Dimethylglycine 1j

Compound 1j is commercially available (Affymetrix, Santa Clara, Calif. 95051, USA, product number T305).

Example 11: Preparation of 3-(Dimethyl(Tetradecyl)Ammonio)Propanoate 1k

Under argon atmosphere, (5-propiolactone (216 mg, 3.0 mmol) is dissolved in a mixture of 4 mL of ether and 2 mL of acetonitrile. N,N-dimethyltetradecylamine (724 mg, 3.0 mmol) is added dropwise over a period of 2 h. The mixture is stirred for another 30 min and the product, a white precipitate, is collected by filtration, washed with several portions of ether and dried in vacuo, yielding 470 mg (50%) of 1k as a white powder. The product is stored below −15° C.

$^1$H-NMR (300 MHz, CDCl$_3$): δ=0.81 (t, J=6.4, 3H). 1.1-1.35 (m, 22H), 1.65 (m, 2H), 2.55 (t. J=7.8, 2H), 3.13 (s, 6H), 3.20 (m, 2H), 3.69 (t, J=7.5, 2H).

MS (ESI): 314.3 (M+H$^+$), 627.5 (2M+H$^+$).

Example 12: Preparation of 3-(Dimethyl(Dodecyl)Ammonio)Propanoate 1m

Under argon atmosphere, β-propiolactone (216 mg, 3.0 mmol) is dissolved in a mixture of 4 mL of ether and 2 mL of acetonitrile. N,N-dimethyldodecylamine (639 mg, 3.0 mmol) is added dropwise over a period of 2 h. The mixture is stirred overnight and the product, a white precipitate, is collected by filtration, washed with several portions of ether and dried in vacuo, yielding 653 mg (76%) of 1m as a white powder. The product is stored below −15° C.

$^1$H-NMR (300 MHz, CDCl$_3$): δ=0.81 (t, J=6.4, 3H). 1.1-1.35 (m, 22H), 1.65 (m, 2H), 2.55 (t, J=7.8, 2H), 3.13 (s, 6H), 3.20 (m, 2H), 3.69 (t, J=7.5, 2H).

MS (ESI): 314.3 (M+H$^+$), 627.5 (2M+H$^+$).

Example 13: Preparation of 4-(Methyl(Tetradecyl)Ammonio)Butanoate 1n

To a solution of 681 mg (3.0 mmol) of N-methyl tetradecylamine in absolute dimelhylformamide (DMF) (6 mL), are added 834 mg (6.0 mmol) of powdered K$_2$CO$_3$ and 1.34 g (6.0 mmol) of 4-bromobutyric acid. The mixture is stirred under argon atmosphere at 130° C. bath temperature for 3 d. The votatiles are removed on a rotary evaporator and the residue purified by preparative HPLC to yield 594 mg (41%) of 4-(methyl(tetradecyl)ammonio)butyric acid tert-butyl ester as a TFA salt. ESI-MS (pos.): 370.3 (M+H$^+$).

4-(methyl(tetradecyl)ammonio)butyric acid tert-butyf ester (241 mg, 0.5 mmol) is suspended in 3 mL of TFA/H$_2$O (95:5). The mixture is stirred for 1 h at room temperature, the volatiles removed on a rotary evaporator and the residue purified by preparative HPLC to yield 114 mg (36%) of 1 n as a white solid.

$^1$H-NMR (300 MHz, CDCl$_3$/CD$_3$ 8:2): δ=0.73 (t, J=6.9, 3H), 1.11 (m), 1.18 (m, Σ=22H), 1.56 (m, 2H), 1.85 (m, 2H), 2.29 (t, J=6.7, 2H), 2.66 (s, 3H). 2.89 (m), 2.97 (m, Σ=4H), 4.05 (br. s, 3H).

MS (ESI): 314.2 (M+H$^+$), 627.4 (2M+H$^+$). Neg.: 312.0 (M−H$^-$).

Example 14: Preparation of 4-(Dimethyl(Tetradecyl)Ammonio)Butanoate 1o

Under argon atmosphere, 4-(methyl(tetradecyl)ammonio)butyric acid tert-butyl ester, TFA salt (described for 1n) (338 mg, 0.70 mmol) is dissolved in acetone (5 ml). Dry powdered K$_2$CO$_3$ (486 mg. 3.5 mmol) and methyl iodide (497 mg, 3.5 mmol) are added and the mixture stirred overnight. The product is purified by preparative HPLC and dried in high vacuum, yielding 266 mg (53%) of 4-(dimethyl(tetradecyl)ammonio)butyric acid tert-butyl ester, TFA salt, 100% pure by HPLC. This material is stirred with 3 ml of TFA/H$_2$O (95:5) for 1 h. HPLC indicated complete conversion. The volatiles are removed on a rotary evaporator and the residue purified by preparative HPLC and dried in high vacuum to yield 105 mg (60%) of 1o.

$^1$H-NMR (300 MHz, CDCl$_3$): δ=0.86 (t, J=6.4, 3H), 1.15-1.35 (m, 22H), 1.69 (m, 2H). 1.98 (m, 2H), 2.41 (t, J=6.1, 2H). 3.06 (s, 6H), 3.17 (m, 2H), 3.34 (m, 2H).

MS (ESI): 328.3 (M+H$^+$), 655.6 (2M+H$^+$).

Example 15: N-Dodecyl-N,N-Dimethylglycine 1p

Compound 1p is commercially available (Affymetrix, Santa Clara, Calif. 95051, USA, product number D350).

Example 16: Preparation of 2-(N-Methyldodecylammonio)Ethanesulfonate 1q

Sodium-2-bromoethane sulfonate (411 mg, 1.95 mmol) and powdered K$_2$CO$_3$ (269 mg, 1.95 mmol) are suspended in 3 mL of dry DMF under argon atmosphere. N-methyldodecylamine (298 mg, 1.50 mmol) is added and the mixture stirred at 130° C. overnight. The volatiles are removed on a rotary evaporator and the residue purified by preparative HPLC and dried in high vacuum to yield 342 mg (74%) of 1q as a white solid.

$^1$H-NMR (300 MHz, CDCl$_3$); δ=0.81 (t, J=6.4, 3H), 1.10-1.35 (m, 18H), 1.70 (m, 2H), 2.88 (s), 2.89 (s, Σ=3H), 3.0-3.45 (m, 5H), 3.55 (m, 1H), 8.46 (br. s, 1H), 8.89 (br. s, 1H).

MS (ESI): 308.2 (M+H$^+$), 325.3 (M+NH$_4^-$), 615.4 (2M+H$^+$).

Example 17: Preparation of 2-(N,N-Dimethyldodecylammonio) Ethanesulfonate 1r A mixture of 2-(N-methyldodecylammonio)ethanesulfonate 1q (225 mg, 0.73 mmol), methyl iodide (568 mg, 4.0 mmol), potassium carbonate (207 mg, 15 mmol) and acetone (5 mL) is stirred under argon atmosphere for 2.5 d. The volatiles are removed and the residue is purified by preparative HPLC and dried in high vacuum to yield 161 mg (68%) of product 1r.

$^1$H-NMR (300 MHz, CDCl$_3$/CD$_3$OD 8:2): δ=0.80 (t, J=6.5, 3H), 1.18/1.29 (2m, Σ=18H), 1.68 (m, 2H), 3.02 (s, 6H), 3.20 (m, 4H), 3.61 (m, 2H).

MS (ESI): 322.2 (M+H$^+$), 643.5 (2M+H$^+$), 660.5 (2M+NH$_4^+$, 665.5 (2M+Na$^+$).

Example 18: Preparation of 2-(N-Methyltetradecylammonio)Ethanesulfonate 1s

A mixture of sodium-2-bromoethanesulfonate (411 mg, 1.95 mmol), N-methyltetradecylamine (342 mg, 1.50 mmol), K$_2$CO$_3$ (269 mg, 1.95 mmol) and DMF (3 mL) is stirred at 135° C. bath temperature under argon atmosphere overnight. The volatiles are removed on a rotary evaporator and the residue purified by preparative HPLC to yield 324 mg (64%) of 1s. $^1$H-NMR (300 MHz, CDCl$_3$): δ=0.90 (t, J=6.4, 3H), 1.15-1.45 (m, 22H), 1.78 (m, 2H), 2.97/2.99 (2s, Σ=3H), 3.05-3.55 (m, 5H), 3.64 (m, 1H), 7.36 (br. s, 1H).

MS (ESI): 336.3 (M+H$^+$), 671.5 (2M+H$^+$), 693.5 (2M+Na$^+$), 709.5 (2M+K$^+$).

Example 19: Preparation of 3-(N,N-Dimethyldodecylammonio)Propylphosphonic Acid 1t Under argon atmosphere, diethyl(3-bromopropyl)phosphonate (1.50 g. 5.75 mmol) is dissolved in 5 mL of absolute ether. N,N-dimethyldodecylamine (1.07 g, 5.00 mmol) is added and the mixture stirred overnight. The volatiles are removed and the residue dried in vacuo, resulting in solidification. The hygroscopic solid is broken up and triturated with ether and the ether removed by suction filtration. The residue is dried in high vacuum to yield 1.46 g (62%) of 3-(N,N-dimethyldodecylammonio)propylphosphonic acid diethylester (bromide salt) as a white, hygroscopic solid.

$^1$H-NMR (300 MHz, CDCl$_3$): δ=0.81 (t, J=6.4, 3H), 1.19 (m), 1.27 (t, J=7.05, Σ=24H), 1.67 (m, 2H), 1.81 (d/t, J=18.1/6.8, 2H), 2.00 (m, 2H), 3.36 (s, 6H), 3.42 (m, 2H), 3.73 (m, 2H), 4.04 (m, 4H).

MS (ESI): 392.4 (M+H$^+$). 3-(N,N-dimethyldodecylammonio)propylphosphonic acid diethylester, bromide salt (175 mg, 0.37 mmol) is placed under argon atmosphere, Absolute dichloromethane (3 mL), bromotrimethylsilane (233 μL, 1.8 mmol) and allyltrimethylsilane (143 μL, 0.9 mmol) are added and the mixture stirred at room temperature for 2.5 d. The volatiles are removed on a rotary evaporator and the residue purified by preparative HPLC to yield 106 mg (85%) of 1t.

$^1$H-NMR (300 MHz, CDCl$_3$/CDCl$_3$ 8:2): δ=0.78 (t, J=6.3, 3H), 1.1-1.3 (m, 18H), 1.62 (m, 4H), 2.10 (m, 2H), 2.97 (s, 6H), 3.13 (m, 2H), 3.27 (m, 2H).

MS (ESI): 336.2 (M+H$^+$), 671.5 (2M+H$^+$).

Example 20: Preparation of 3-(N-Methyl-N—Hexadecylamino)Propylphosphonic Acid Diethylester Hydrobromide 1w Under argon atmosphere, N-methylhexadecylamine (510 mg, 2.0 mmol) is partially dissolved in absolute ether (4 mL). Diethyl(3-bromopropyl)phosphonate (647 mg, 2.50 mmol) and diisopropylethylamine (436 jjL, 2.5 mmol) are added and the mixture stirred overnight at room temperature. The volatiles are removed and the residue purified by flash chromatography on silica using dichloromethane/methanol 10:1 to yield 216 mg (21%) of 1w.

¹H-NMR (300 MHz, CDCl$_3$): δ=0.81 (t, J=6.3, 3H), 1.19 (m), 1.25 T, J=6.9, Σ=32H), 1.40 (m, 2H), 1.72 (m, 4H), 2.18 (s, 3H), 2.31 (m, 2H), 2.39 (br. t, J=6.5, 2H), 4.02 (m$_c$, 4H).
MS (ESI): 434.4 (M+H$^+$). 889.7 (2M+Na$^+$).

Example 21: Preparation of 3-(N-Methyl-N—Hexadecylamino)Propylphosphonic Acid 1v Under argon atmosphere, a mixture of 3-(N-methyl-N-hexadecylamino)propylphosphonic acid diethylester hydrobromide (1w) (130 mg, 0.25 mmol), absolute dichloromethane (2 mL), bromotrimethylsilane (184 mg, 1.20 mmol) and allyltrimethylsilane (68 mg, 0.60 mmol) is stirred overnight at room temperature. The volatiles are removed and the residue purified by preparative HPLC to yield 52 mg (55%) of 1v.
¹H-NMR (300 MHz, CDCl$_3$/CD$_3$OD 8:2): δ=0.89 (t, J=6.5, 3H), 1.2-1.4 (m, 26H), 1.65-1.87 (m, 4H), 2.06 (m, 2H), 2.80 (s, 3H), 2.85-3.25 (br. m, 4H).
MS (ESI): 378.3 (M+H$^+$), 755.6 (2M+H$^+$).

Example 22: Preparation of 3-(N-Methyl-N-Tetradecylamino)Propylphosphonic Acid Diethyiester Hydrobromide 1x N-methyltetradecylamine (454 mg, 2.0 mmol) is dissolved in absolute ether (3 mL) under argon atmosphere. Diisopropylethylamine (322 mg, 2.5 mmol) and diethyl(3-bromopropyl)phosphonate (647 mg, 2.5 mmol) are added and the mixture stirred for 2.5 d at room temperature. A precipitate Is removed and the supernatant concentrated on a rotary evaporator and purified by flash chromatography on silica using dichoromethaneAnethanol (10:1) to yield 356 mg (26%) of 1x a white solid.
¹H-NMR (300 MHz, CDCl$_3$): δ=0.81 (t, J=6.9, 3H), 1.19 (m), 1.25 (t, J=7.1, Σ=28H), 1.40 (m, 2H), 1.71 (m, 4H), 2.18 (s, 3H), 2.31 (m, 2H), 2.39 (br. t, J=7.2, 2H), 2.95 (br. s, 1H), 4.02 (m$_c$, 4H).
MS (ESI): 406.4 (M+H$^+$), 833.6 (2M+Na$^+$).

Example 23: Preparation of 3-(N-Methyl-N-Tetradecylamino)Propylphosphonic Acid (Betaine) 1u 3-(N-methyl-N-tetradecylamino)propylphosphonic acid diethylester hydrobromide 1x (162 mg, 0.33 mmol) is dissolved in 2 mL of absolute dichloromethane under argon atmosphere. Trimethylsilyl bromide (245 mg, 1.6 mmol) and allyltrimethylsilane (91 mg, 0.8 mmol) are added and the mixture stirred overnight at room temperature. The volatiles are removed on a rotary evaporator and the residue dissolved in ethanol and purified by preparative HPLC to yield 105 mg (91%) of 1u as a white solid.
¹H-NMR (300 MHz, CDCl$_3$): δ=0.81 (t, J=6.9, 3H), 1.1-1.3 (m, 20H), 1.61 (br.s, 2H), 1.75 (m, 2H), 2.00 (m, 2H), 2.73 (s, 3H), 2.86 (m), 3.02 (m). 3.14 (m, Σ=4H).
MS (ESI): 350.3 (M+H$^+$)r 699.6 (2M+H$^+$). Neg.: 697.3 (2M–H$^+$).

Examples 24 and 25: Preparation of N—Hexadecyl-N-(3-Sulfonatopropyl)Piperidinium 2a and 1-Hexadecyl-1-(3-Sulfonatopropyl)-4-Hydroxypiperidinium 2b Piperidine (1.32 g, 15.5 mmol) and 1-iodohexadecane (1.82 g, 5.17 mmol) are dissolved in 6-8 mL of ethanol and stirred overnight while shielded from light. The mixture is partitioned between plenty of ether and dilute NaOH, washed with sat. NaCl once, dried over Na$_2$SO$_4$, rotavapped down to an oil and dried in vacuo. Yield: 1.45 g (90% of brownish oil). The product is used in the next step without further purification.

In 4 mL of EtOAc, N-hexadecylpiperidine (300 mg, 0.97 mmol) is mixed with 1,3-propanesultone (142 mg, 1.63 mmol). The mixture is stirred first at room temperature (2 d), then at 50° C. overnight. After addition of another 142 mg of 1,3-propanesultone, the mixture is stirred at reflux for 2 days, at which point analytical HPLC indicates complete conversion. The volatiles are removed and the residue is purified by preparative HPLC to yield 298 mg (71%) of pure 2a as a white solid.
¹H-NMR (300 MHz, CDCl$_3$): δ=0.81 (t, J=7.8, 3H). 1.1-1.4 (m, 26H), 1.5-1.8 (m, 6H), 1.91 (m, 2H), 2.14 (m, 2H), 2.91 (t, J=6.2, 2H), 3.16 (m, 2H), 3.29 (m, 2H), 3.45 (M, 2H), 3.64 (m, 2H).
MS (ESI): 432.4 (M+H$^+$), 863.8 (2M+H$^+$).
Compound 2b is prepared in a similar way using 4-hydroxypiperidine instead of piperidine.

Example 26: Preparation of Trans-N-Tetradecyl-N-(3-Sulfonatopropyl)-3-Diethylaminocarbonyl-Piperidinium 2c A mixture of N,N-diethyl-3-piperidinecarboxamide (809 mg, 4.4 mmol), ethanol (3 mL) and tetradecyl iodide (620 mg, 1.9 mmol) is stirred overnight at room temperature. HPLC shows complete conversion. The mixture is diluted with ether (200 mL) and extracted with 1N NaOH (1x 100 mL) and saturated NaCl (1x 100 mL) and the organic layer dried over Na$_2$SO$_4$ and filtered. The volatiles are removed and the residue purified by flash chromatography on silica using dichloromethane/methanol (10:1). The product is dried in vacuo to yield 682 mg (94%) of 1-tetradecyl-3-diethylaminocarbonylpiperidine. The product contains residual N,N-diethyl-3-piperidinecarboxamide, which is removed in the next step.
MS (ESI): 381.4 (M+H$^+$).

A mixture of 1-tetradecyl-3-diethylaminocarbonylpiperidine (380 mg, 1.0 mmol), ethyl acetate (3 mL) and 1,3-propanesultone (488 mg, 4.0 mmol) is stirred under argon atmosphere under reflux for 6 d. HPLC shows conversion is incomplete and the cis- and trans-stereoisomers give rise to two closely eluting peaks. The volatiles are removed and the residue purified by preparative HPLC. The two resulting fractions are purified again by preparative HPLC, yielding the racemic cis- and trans-stereoisomer in 95% purity, with a yield of 71 mg (14%) of trans-stereoisomer 2c and 54 mg (11%) of the cis-stereoisorner.
¹H-NMR (125 MHz, CDCl3): δ=0.81 (t, J=6.4, 3H), 1.03 (t, J=7.1, 3H), 1.10-1.35 (m, 25H), 1.50 (m, 1H), 1.60-1.90 (m, 3H), 1.90-2.20 (m, 3H), 2.20-2.45 (m, 1H), 2.85-3.15 (m, 5H), 3.15-3.55 (m, 7H), 3.60 (br. d, J=12.2, 1H), 3.75-3.95 (m, 3H).
¹³C-NMR and DEPT (125.7 MHz, CDCl$_3$): 12.73 (CH$_3$), 14.09 (CH$_3$), 14.74 (CH$_3$), 18.15 (CH$_2$), 18.88 (CH$_2$), 21.60 (CH$_2$), 22.66 (CH$_2$), 25.91 (CH$_2$), 26.37 (CH$_2$), 28.99 (CH$_2$), 29.32 (CH$_2$), 29.38 (CH$_2$), 29.52 (CH$_2$), 29.60 (CH$_2$), 29.62 (CH$_2$), 31.88 (CH$_2$), 32.92 (CH), 40.51 (CH$_2$), 40.51 (CH$_2$), 42.15 (CH$_2$), 47.09 (CH$_2$), 53.80 (CH$_2$), 59.20 (CH$_2$), 60.64 (CH$_2$). 65.23 (CH$_2$), 170.09 (CO).
MS (ESI): 503.5 (M+H$^+$).

Example 27: Inhibition of Mast Cell Degranulation

Introduction

Mast cells are key effector cells involved in allergic and inflammatory diseases, and the Rat Basophilic Leukemia clone 2H3 (RBL-2H3) cell line is a commonly used model of allergen dependent immune modulator release (degranulation) in mast cells. On their surface, they express the high affinity receptor for IgE (FcεRI). Upon binding of antigen-specific IgE to the receptor, cells become sensitized to the IgE specific antigen (allergen). When IgE-sensitized cells then encounter multivalent antigen, the antigen clusters IgE-FcεRI complexes and initiates a signal transduction cascade that leads to degranulation, that is, the release of inflammatory mediators, such as cytokines, eicosanoids, histamine and enzymes. The assay can be used as a screening method to identify immune-modulating compounds, in particular compounds useful in the medical management of allergic and inflammatory diseases and asthma, β-hexosaminidase was previously shown to be released with the same kinetics as histamine (Schwartz et al., J Immunology; 123:1445-1450 (1979)), thus offering a simple means to monitor degranulation. The RBL-2H3 cell line has been successfully used to identify compounds with anti-allergic activity (Choo et al. Planta Med., 69:518-522 (2003)).

Materials and Methods

Materials Chemicals: Rat anti-DNP IgE monoclonal antibody was acquired from Biozol (BZL06936), dinitrophenyl-conjugated human serum albumin (A6661) and Triton X-100 (T9284) were from Sigma-Aldrich, 4-methylumbelliferyl-N-acetyl-β-D-glucosaminide (474502), Phorbol-12-myristate-13-acetate (524400) and thapslgargin (586005) from Calbiochem. Ionomycin (ALX-450-006) was purchased from Alexis Biochemicals. DMSO was from Merck (1.02950.0500) or Sigma-Aldrich (D2650). Cell culture media and supplements, Minimum Essential Medium (21090-022), Minimum Essential Medium without Phenol Red (51200-046), RPMI 1640 Medium (31870-025), L-Glutamine (25030-24) and 0.05% Trypsin-EDTA (25300-054), were obtained from Invitrogen. Fetal bovine serum (A15-151) was from PAA Laboratories. Other reagents were standard laboratory grade or better.

Buffers and solutions: Phosphate buffered saline (PBS) and 1 M HEPES were provided by the in-house service facility. Tyrode's buffer (TyB) consisted of Minimum Essential Medium without Phenol Red supplemented with 2 mM L-gtutamine and 20 mM HEPES. Lysis buffer consisted of 25 mM Tris-HCl, pH 7.5, 150 mM NaCl, 5 mM EDTA and 0.1% (w/v) Triton X-100. DNP—HSA was dissolved to 1 mg/ml in water. MUG substrate solution consisted of 2.5 mM 4-methylumbelliferyl-N-acetyl-β-D-glucosaminide in 0.05 M citrate, pH 4.5; stop solution was 0.1 M $NaHCO_3$/0.1 M $Na_2CO_3$, pH 10.

Consumables and equipment: For small-volume liquid handling procedures, Rainin LTS electronic pipettes were routinely used (Mettler-Toledo). Costar-Corning 24-well plates (3337) were centrifuged in an Eppendorf 5804 R centrifuge. A Heraeus B15 table top incubator was used for incubations at 37° C. under non-sterile conditions. Fluorescence was measured in black Nunc 96-well plates (237105) using a microplate reader (Tecan Safire) or FlexStation 3 (Molecular Devices) multi-mode plate reader. Cells were maintained in Hera Cell 240 $CO_2$ incubators (Thermo Scientific). Serological pipettes (4487, 4488 and 4489) and cell culture flasks (431080) were from Coming-Costar, 1.5 and 2 ml microcentrifuge tubes (0030 120.086 and 0030 120.094) were from Eppendorf.

Cell Culture: RBL-2H3 cells obtained from the German Collection of Microorganisms and Cell Cultures (ACC312) (Braunschweig, Germany) were maintained in 70% Minimum Essential Medium with Earle's Salts, 20% RPMI 1640 Medium, 10% FBS and 2 mM l-glutamine in 95% air/5% $CO_2$ at 37° C. and routinely checked for mycoplasma contamination. Cells were passaged every 3-4 days; after washing cells once with 35 ml PBS cells were incubated 8 min with 5 ml 0.05% Trypsin-EDTA solution at 37° C. Cells were removed from the incubator, 15 ml culture medium was added and cells were resuspended by repeated pipetting.

Cell seeding: cells were harvested with Trypsin-EDTA as described and 50-100 μl cell suspension seeded Into Costar CellBind 24 well cluster plates (no. 3337). Plates were kept for 30 min at RT under the sterile hood before being transferred to the incubator. Cells were used within one or two days after seeding.

Measurement of β—Hexosaminidase Release

Experimental Procedures

For sensitization, cells for immediate use were sensitized 6-12 h after plating; cells to be used the following day were sensitized 26-38 h after plating. Culture plates were removed from the incubator and checked for cell growth and contamination. The medium was discarded and cells were sensitized with anti-DNP IgE (0.4 μg/ml) in 0.4 ml culture medium overnight. Following overnight sensitization, cells were washed with 0.8 ml pre-warmed TyB and 0.38 ml test compound or vehicle control (supplemented or not with 1% FBS) were added to duplicate wells. Samples were adjusted to contain 1% vehicle for test compounds dissolved in organic solvents. Cells were incubated for 1 h at 37° C. At the end of the incubation period, cells were routinely stimulated with 20 μl DNP-HSA (2 μg/ml; final concentration 0.1 μg/ml) diluted in TyB and cells were incubated for 15 min at 37° C. Alternatively, cells were stimulated with 20 μl μM ionomycin (final concentration 0.25 μM) or 20 nM PMA thapsigargin (final concentration 0.25 μM), both in the absence or presence of 20 nM PMA (final concentration).

Plates were removed from the incubator and immediately centrifuged at 4° C. for 5 min at 250×g and transferred to an ice bath. Aliquots of supernatants, 25 μl, were transferred to 96-well plates. Remaining supernatant was aspirated from control wells and cells were lysed in 400 μm lysis buffer for 5 min at RT on an orbital shaker at 450 rpm under non-sterile conditions. After lysis, 25 μl aliquots of lysates were transferred to 96-well plates.

MUG substrate solution, 100 μl, were added to supernatant and lysate samples and plates were incubated 30 min at 37° C. The reaction was terminated by addition of 150 μl stop solution. Fluorescence was measured at 365 nm excitation and 440 nm emission wavelengths.

Test compound preparation: test compounds were prepared in 1.5 or 2 ml microcentrifuge tubes and incubated for 30 min at 37° C. in a Thermomixer Comfort with agitation (750 rpm). An electronic multichannel pipette was used for rapid transfer of compound dilutions from microcentrifuge tubes to the cells.

Controls: controls used are defined as follows: negative control, supernatant of unstimulated cells was measured for unspecific β-hexosaminidase release; positive control, supernatant of DNP-HSA stimulated cells was measured for specific, antigen-stimulated β-hexosaminidase release;

maximum control, lysate of unstimulated cells was measured for total β-hexosaminidase content.

Assessment of Pharmacologic Effect

Degranulation (β-hexosaminidase release): Degranulation was calculated as the percentage of β-hexosaminidase released with respect to maximum control (total β-hexosaminidase) after subtraction of negative control (unspecific release) using the formula;

% Degranulation=100×(test compound-negative control)/(maximum control-negative control)

% Inhibition of degranulation (inhibition of β-hexosaminidase release): Inhibition of degranulation was calculated as percent reduction of β-hexosaminidase release with respect to positive control (antigen-stimulated release) after subtraction of negative control (unspecific release) using the formula;

% Inhibition=100×(1−(test compound-negative control)/(positive control-negative control))

Measurement of Maximum Tolerated Concentration

The maximum tolerated concentration (MTC), i.e. the highest concentration of test compound that does not cause cytotoxicity, as determined by the release of lactate dehydrogenase, was measured over the tested concentration range. A commercially available cytotoxicity test was used (Promega Cytotox-One cat. #67891).

The safety index (SI) of a test compound Is the ratio between the maximum tolerated concentration and the 1C50 and is used as a measure of the relative safety of the test compound.

Results

Concentration-dependent inhibition of degranulation was determined for ail test compounds over a concentration range, as shown in FIG. 1, and IC50 values (concentration at which 50% of maximal inhibition is reached) were determined for each compound together with the MTC values over the same concentration range (Table 1). Results are taken from at least three independent experiments.

TABLE 1

Inhibition of degranulation: IC50, MTC and SI values

| Compound | IC50 (μM) | MTC (μM) | SI |
| --- | --- | --- | --- |
| 1a | 3.2 | 100 | 31.3 |
| 1b | 4.3 | 100 | 23.3 |
| 1c | 2.8 | 200 | 71.4 |
| 1d | 3.9 | 100 | 25.6 |
| 1e | 3.7 | 150 | 40.5 |
| 1f | 4.0 | 75 | 18.8 |
| 1g | 9.5 | 50 | 5.3 |
| 1h | 3.7 | 50 | 13.5 |
| 1i | 4.1 | 200 | 48.8 |
| 1j | 5.1 | 75 | 14.7 |
| 1k | 5.3 | 100 | 18.9 |
| 1m | 73% inhibition at 25 μM | 100 | — |
| 1n | 8.0 | 100 | 12.5 |
| 1o | 65% inhibition at 25 μM | 100 | — |
| 1p | 50% inhibition at 25 μM | 100 | — |
| 1q | 8.8 | 200 | 22.7 |
| 1r | 4.2 | 200 | 47.6 |
| 1s | 5.6 | 100 | 17.9 |
| 1t | 6.1 | 200 | 32.8 |
| 1u | 5.9 | 200 | 33.9 |
| 1v | 8.8 | 200 | 22.7 |

TABLE 1-continued

Inhibition of degranulation: IC50, MTC and SI values

| Compound | IC50 (μM) | MTC (μM) | SI |
| --- | --- | --- | --- |
| 1w | 6.9 | 200 | 29.0 |
| 1x | 5.5 | 100 | 18.2 |
| 2a | 4.5 | 50 | 11.1 |
| 2b | 4.3 | 50 | 11.6 |
| 2c | 50% inhibition at 25 μM | 100 | — |
| Miltefosine | 4.2 | 25 | 6.0 |

The MTC of the test compounds was 5-70 fold higher than their respective IC50s and hence, the inhibition of degranulation can be ascribed to a pharmacological effect and not to an effect secondary to cytotoxicity.

All substances outlined in Table 1 show IC50 values in the low micromolar range combined with high MTC values when compared to Miltefosine. Thus, the compounds according to the invention and, in particular compounds 1a to 1x and compounds 2a to 2c, have an advantageously low cytotoxicity.

Mast cell degranulation is a key cellular event in allergic and inflammatory reactions, in particular in pathological events involving the release of mediators such as histamine, leukotrienes and prostaglandins as well as proteases. As consequence, the inhibition of mast cell degranulation is a valuable strategy for prevention or treatment of pathological processes involving the aforementioned mediators. Furthermore, the mast cell degranulation assay provides an estimate of the activity of test compounds in other cells that play a key role in the inflammatory response, such as granulocytes, macrophages and thymocytes, which release proinflammatory cytokines and chemokines and tissue eroding proteases.

Example 28: Inhibition of Activation of Akt Kinase

Introduction

The mast cell degranulation assay using the RBL-2H3 cell line (see Example 27) was also used to determine the status of the PI3K/Akt axis. Activation of PI3K leads to production of PIP3 on the cytosolic side of the lipid bilayer. Akt is recruited to the PIP3 domain and subsequently activated by phosphorylation on residues Ser473 and Thr308. (Franke et al., Cell 81:727-736, (1995)). Once recruited to the membrane, it is phosphorylated and activated by other kinases (Hemmings, Science 275:628-630 (1997); Hemmings. Science 276:534 (1997); Downward, Science 279:673-674 (1998); Alessi et al., EMBO J. 15:6541-6551 (1996)). Western blotting of the phosphorylated Ser473 residue on Akt (phospho-Akt Ser473) is widely used to assess the level of activation of the PI3K/Akt axis.

Materials and Methods

Materials

All buffers and solutions used for the phosphor-Akt Ser473 assay were from Meso Scale Discovery. Tris Lysis Buffer consisted of 150 mM NaCl, 20 mM Tris, pH 7.5, 1 mM EDTA, 1 mM EGTA and 1% Triton-X-100. Complete Tris Lysis Buffer was prepared prior to use by addition of protease inhibitor, phosphatase inhibitors and PMSF. The 10x Tris Wash Buffer consisted of 500 mM Tris, pH 7.5, 1.5 M NaCl and 0.2% Tween-20. Blocker A was made up of bovine serum albumin in Tris Wash Buffer. Read Buffer T was used according to manufacturer's instructions. The Whole Cell Lysate Kits used were phospho-Akt Ser473 (K11100D. Lot K0011749) and total ERK½ (K11107D, Lot K0011698) as a loading control.

Equipment 12-well multichannel pipettes (30-300 μl) from Eppendorf were used. Assay plates were agitated on a TiMix 5 control (Edmund Buhler). Electrochemiluminescence detection was performed on a SECTOR Imager 6000 (Meso Scale Discovery).

Measurement of Phospho-Akt Ser473

Experimental Procedures

Protein assay: protein concentration was determined using the BCA (bicinchoninic acid) Protein Assay kit according to the manufacturer's instructions, Briefly, duplicate 10 μl samples of bovine serum albumin (BSA) standards, blank and lysates were incubated in a 96-well plate with 0.2 ml working reagent for 30 min at 37° C. Plates cooled to room temperature for 5 min and absorbance at 562 nm measured in a multi-mode plate reader. Protein concentrations were calculated using FlexStation 3 software (SoftMax Pro version 5.3). Protein concentration of lysates was determined from a standard curve (BSA) using a linear curve fit.

Phosphoprotein assay: protein phosphorylation was determined using the MULTI-SPOT® Assay System (Meso Scale Discovery), providing simultaneous detection of phosphorylated and total proteins. Briefly, capture antibodies against phosphorylated and total protein are patterned on distinct spots in the same well of 96-well plates. Sandwich immunoassay and electrochemiluminescence detection technology are combined to measure intensity of the emitted light from phosphorylated and total protein spots. For analysis of phosphor-Akt Ser473 was performed according to the manufacturer's instructions. The optimal amount of protein was determined at 5 μg lysate per well for ERK½ and 10 μg/well for phospho-Akt Ser473. Plates were blocked with 25 μl/well Blocker A for 1 h at room temperature with gentle agitation. During this time, the lysates were thawed and diluted to the desired protein concentration in complete Tris Lysis Buffer. Plates were washed four times in Tris Wash Buffer and 25 μl lysate per well added. Plates were incubated for 1-3 h at room temperature with agitation according to the manufacturer's recommendations. Plates were washed four times with Tris Wash Buffer, followed by addition of 25 μl/well of the respective detection antibody and incubation for 1 h at room temperature, with agitation. After a final four washes with Tris Wash Buffer 150 μl/well, Read Buffer T was added, and plates read on a SECTOR Imager 6000 plate reader.

Assessment of Effects of Phospho-Akt Ser473

The mean background signal from each plate was subtracted from averaged raw data. The amount of total protein phosphorylaled was expressed as % phosphoprotein according to the manufacturer's (Meso Scale Discovery) Instructions.

Results

Levels of phospho-Akt Ser473 were determined in IgE sensitized and antigen stimulated cells after treatment without (positive control) or with 1, 5 and 25 μM test compound and normalized to levels of total Akt. Concentration-dependent inhibition of Akt phosphorylation on Ser473 was demonstrated, as shown in FIG. 2. Table 2 shows levels of normalized phospho-Akt Ser473 as a percentage of those in the positive control.

TABLE 2

Inhibition of Akt phosphorylation on Ser473 by compounds 1a and 1c

| Compound | Level of phospho-Akt Ser473 (% positive control) | | |
|---|---|---|---|
| | 1 μM | 5 μM | 25 μM |
| 1a | 103.1 ± 17.4 | 57.0 ± 15.2 | 13.2 ± 4.2 |
| 1c | 83.2 ± 17.3 | 11.7 ± 7.7 | 2.2 ± 1.4 |

Percentage of total Akt phosphorylated on Ser473 expressed as percentage of control untreated cells, after Induction with IgE and antigen for 15 min.

A dose-dependent decrease in levels of phospho-Akt Ser473 was observed after treatment with all compounds outlined in Table 2. Thus, the compounds according to the invention can be used to reduce levels of activated Akt and, accordingly, are useful in the medical intervention in indications in which hyperactivated Akt plays a pathogenic role, such as inflammatory and allergic diseases.

Example 29: Inhibition of the Delayed-Type Hypersensitivity (DTH) Reaction in Mice Introduction The anti-inflammatory and anti-allergic effects of compound 1a was assessed in a mouse model of skin delayed-type hypersensitivity (DTH) reactions and compared to a vehicle control and to the reference drug dexamethasone. DTH reactions are antigen-specific cell-mediated immune responses, driven primarily by T helper type 1 (Th1) cells, similar to the tuberculin immunization response. The immune reaction induced by an ovalbumin challenge to animals previously sensitized with ovalbumin in Complete Freud's Adjuvant, is characterized by swelling (edema) at the site of challenge, e.g. the mouse ear. Dexamethasone, an anti-inflammatory steroid, reduces cell-mediated immune responses and was employed to validate the responsiveness of the assay to pharmacological treatment.

Materials and Methods

Materials

Ovalbumin (fraction V, lyophilized powder), complete Freud's adjuvant (CFA) and methylcelluiose were obtained from Sigma-Aldrich, dexamethasone from Pharmaceutical Works Polfa (Pabianice, Poland).

Animals

Female BALB/cJW mice were bred at the University of Lodz, Lodz, Poland and housed in groups of 8 in makrolon cages with a 12 h light-dark cycle. Mice were given free access to food (Agropol S. j., Motycz, Poland) and water.

Antigen Sensitization and Challenge

Group size was n=8 mice unless otherwise stated. Test compound was freshly prepared before administration.

Sensitization: The protein antigen, ovalbumin, was reconstituted in PBS at 4 mg/ml. An ovalbumin-CFA emulsion was prepared by mixing the protein solution with the CFA suspension at a ratio of 1:1, using two Luer-lock syringes. The emulsion was tested by putting a drop of emulsion onto PBS; if the emulsion remained as a light droplet on the PBS, the emulsion was deemed ready. Mice were sensitized by subcutaneously injecting 25 μL of emulsion into each side of the tail (100 μg ovalbumin per mouse).

Challenge: On the sixth day after sensitization, DTH was elicited by challenging animals subcutaneously (gauge 30 needle, B. Braun Melsungen, Melsungen, Germany) in the left ears with 10 μL of a 1% suspension of heat-aggregated ovalbumin (HOVA) (100 μg ovalbumin per mouse). The right ears were administered subcutaneously with PBS and served to determine the individual differences in ear thicknesses. HOVA was prepared by heating a 5% solution of ovalbumin in saline for 1 h at 80° C. with occasional swirling. After cooling to room temperature and centrifugation (400 g, 10 min at 4° C.), the pellet was washed twice with saline, resuspended at 2% in PBS and aliquots stored at −30° C. Before injection, HOVA was diluted with an equal volume of PBS and sonicated. Ear thickness was measured with a precise spring-loaded caliper (Art. No, 7309, Mltutoyo, Kawasaki, Japan) before challenge, and 24 h after challenge.

Sensitization, challenge and ear thickness measurement were performed under anesthesia (ketamine 80 mg/kg plus xylazine 8 mg/kg, intraperitoneal).

Compound Administration

The anti-inflammatory effects of compound 1a were compared to a vehicle control (0.5% methyl cellulose solution) and to the reference drug, dexamethasone. Test compound was given orally by gavage (Art. No. 432093, Harvard Apparatus GmbH, March-Hugstetten, Germany) as follows: 16 h prior to ovalbumin sensitization, a loading dose of 100 mg/kg was administered; the first maintenance dose of 25 mg/kg was given 3 h before sensitization (day 0) and on each of the next five consecutive days (day 1 to 5) as well as on the day of antigen challenge (day 6) (a total of 8 administrations). Three hours after the last dose, the antigen challenge was performed on the ears as described above. Dexamethasone was given at 1 mg/kg orally by gavage 3 h before sensitization and once daily with the final dose given 3 h prior to antigen challenge (a total of 7 administrations). All administrations were given in a volume of 10 mL/kg.

Quantification of Assay Results

To account for individual variability, the increase in right ear thickness, before and 24 h after administration of PBS, was subtracted from the HOVA-induced increase in left ear thickness. The increase in ear thickness was calculated by the difference between ear thickness before and 24 h after antigen challenge. Percent inhibition of ear swelling was calculated according to the following formula;

$$\% \text{ inhibition} = 100 \times (\text{IET}_{vehicle} - \text{IET}_{compound}) / \text{IET}_{vehicle}$$

where $\text{IET} = (\text{ET}_{24\ hrs\ pc} - \text{ET}_{predose})_{HOVA\text{-}treated\ ears} - (\text{ET}_{24\ hrs\ pc} - \text{ET}_{predose})_{PBS\text{-}treated\ ears}$ (IET, increase ear thickness; ET, ear thickness; pc, post challenge)

Statistical Evaluation

Mean and standard deviation (SD) were calculated from individual ear edema values. Statistical evaluation was a one-way analysis of variance (ANOVA) with Dunnett's post hoc test or Student's t-test where appropriate.

Results

Suppression of mouse ear swelling by compound 1a and dexamethasone, compared to vehicle control is shown in FIG. 3, Table 3 summarizes the inhibition of DTH for compounds 1a.

TABLE 3

Effect of compound 1a on ear swelling in the DTH response in mice.

| Compound | Inhibition of mouse ear swelling |
|---|---|
| 1a, 100 mg/kg | 32* |
| Dexamethasone, 1.0 mg/kg | 49* |

*$p < 0.01$ vs. vehicle control (Dunett's post hoc test)

Dexamethasone administered orally at a dose of 1 mg/kg, once daily over the whole sensitization period resulted in a significantly reduced DTH response, with inhibition of 49%. Such high dosing (overdose) is, however, not suitable for treatment of humans due to severe side effects of the corticosteroid and was only used to validate the responsiveness of the model. In addition, in the course of the current study, administration of dexamethasone resulted in a significant loss in body weight of 4.4% ($p<0.01$ vs. vehicle control with the paired Student's t-test), a typical sign of corticosteroid toxicity. In contrast, no toxic side-effects of compound 1a were observed during the course of the study.

Compound 1a, administered orally twice daily over the whole sensitization period at 20 mg/kg (loading dose 100 mg/kg), significantly reduced the DTH response by 32%. Hence, compound 1a was able to produce an inhibition equivalent to 65% that of a high dose of dexamethasone.

The reduction of DTH response obtained by treatment with compound 1a demonstrates that the compounds according to the invention and, in particular compound 1a, are effective in the pharmaceutical intervention in allergic and inflammatory diseases involving antigen-specific cell-mediated immune responses.

Example 30: Inhibition of the Allergic Contact Dermatitis Inflammatory Response in Mice Introduction The anti-inflammatory and anti-allergic effects of compound 1a were assessed in a mouse model of allergic contact dermatitis, a response driven primarily by T helper type 2 (Th2) cells. It has been demonstrated that BALB/c mice are susceptible to the allergen toluene-2,4-diisocyanate (TDI), producing an inflammatory condition of the skin with similar aspects to that of human atopic dermatitis (Baumer et al., J Pharm Pharmacol, 55:1107-1114 (2003); Baumer et al., Br J Dermatol. 151:823-830 (2004); Ehinger et al., Eur J Pharmacol. 392:93-99 (2000)). In this model, an allergic dermatitis response is obtained by sensitizing mice to TDI and subsequently challenging them with antigen by topical administration onto the ears. A quantitative assessment of anti-inflammatory and anti-allergic effects of topically or orally administered test compounds is possible by measuring the resulting ear swelling.

The advantages of the allergic contact dermatitis model (Zdliner et al., Bioessays 26:693-6 (2004)) are reproducibility and reliability (>90% of BALB/c mice respond to sensitization), a short induction protocol, quantitative assessment by measuring ear thickness, atopic dermatitis-like skin lesions can be induced, and clinically relevant pharmaceuticals, such as corticosteroids, calcineurin-inhibitors and PDE4-inhibitors, are effective in this model.

Materials and Methods

Animals

Female BALB/c-mice were obtained from Charles River (Sulzfeld, Germany) at age 8 weeks. All animals were housed in groups of eight per cage at 22° C. with a 12 h light/dark-cycle. Water and a standard diet (Aitromin, Lage/ Lippe, Germany) were available ad libitum. All animals were acclimatized for one week before experimental procedures were commenced.

TDI Sensitization, Allergen Challenge and Mouse Ear Swelling Test

Experimental procedures for BALB/c mice housing, TDI sensitization and challenge, and measurement of ear thickness were performed as previously described (Baurner et al., J Pharm Pharmacol. 55:1107-1114 (2003)) with the following modifications. For active sensitization, 100 µL of 5% (w/v) TDI was administered to the shaved and stripped abdominal epidermis on day one, and for the next three consecutive days, 50 µL of 5% (w/v) TDI was applied. The allergic reaction was boosted 21 days later by application of 50 µL of 0.5% (w/v) TDI. For the examination of test compound effects, the left ears were used for the TDI challenge (20 µL of 0.5% in acetone) and ear thickness measured 3 h before and 24 h after challenge.

Compound Administration for Systemic Treatment

Group size was n=7 mice unless otherwise stated. Test compounds were freshly prepared before administration.

Administration time: to determine optimal time for administration treatment groups were treated orally by gavage with 100 mg/kg of compound 1a (suspended in phosphate-buffered saline (PBS), 10 mL/kg) 4 or 16 h before topical TDI challenge. Vehicle treated mice received PBS (10 mL/kg) orally, 4 h before challenge.

Dose-response: two groups of mice were treated orally with compound 1a at 20 mg/kg or 100 mg/kg suspended in PBS, 4 h before topical TDI challenge. Vehicle treated mice received PBS orally 4 h before challenge.

Compound Administration for Topical Treatment

Compound 1a was administered to two groups of mice topically in 20 µl of a 2% or 6% solution in acetone/water (1:1). The solution was applied, 2 h before topical TDI challenge by administration of 10 µl onto each of the inner and outer surfaces of the left ears. A vehicle group (n=7) was treated with acetone/water (1:1).

Determination of Local Lymph Node Weight and Cell Count

Directly after sacrifice, the ear draining lymph node (Ln. auricufaris) was prepared and excised. Organ weight was determined by means of an analytical balance (Kern, Balingen, Germany). Single cell suspensions were prepared by means of a glass potter (VWR, Darmstadt, Germany) and cells were counted with a hemocytometer (Neubauer, V W R, Germany).

Statistical Evaluation

Mean and standard error of the mean (SEM) were calculated from individual ear edema values. Statistical evaluation was a one-way analysis of variance (ANOVA) (if the test for normal distribution was passed) or the Kruskal-Wallis one-way ANOVA on Ranks (if the normal distribution test failed), Both were followed by a post-hoc test (Dunnett's method or Dunn's test, respectively). A $p<0.05$ was considered to be significant.

Results

Suppression of mouse ear swelling by compound 1a after oral administration, compared to vehicle control is shown in FIG. 4A. Table 4 summarizes inhibition of the allergic contact dermatitis response by compound 1a.

TABLE 4

Effect of orally administered compound 1a or ear swelling in the allergic contact dermatitis response in mice.

| Compound<br>Administration time (oral) | Inhibition of mouse ear swelling |
|---|---|
| 1a, 100 mg/kg, 4 h | 51.7* |
| 1a, 100 mg/kg, 16 h | 32.2 |

*$p < 0.05$ vs. vehicle control (Dunnett's post hoc test) compared to vehicle

In the administration time study with oral administration, compound 1a reduced ear swelling significantly (52% of vehicle control) when administered 4 h before challenge, as also shown in FIG. 4A.

Compound 1a had a significant impact on the TDI induced inflammatory reaction in a pilot study at 100 mg/kg. Thus, the compounds according to the invention and, in particular compound 1a, are particularly effective and thus useful for the oral pharmaceutical intervention in inflammatory diseases, in particular in atopic dermatitis. Suppression of mouse ear swelling by compound 1a after topical administration, compared to vehicle control is shown in FIG. 4B, Table 5 summarizes inhibition of the allergic contact dermatitis response by compound 1a.

TABLE 5

Effect of topically administered compound 1a on ear swelling in the allergic contact dermatitis response in mice.

| Compound | Inhibition of mouse ear swelling |
|---|---|
| 1a, 2% | 72.0*** |
| 1a, 6% | 86.0*** |

***$p < 0.001$ vs. vehicle control (Dunnett's post hoc test) compared to vehicle Compound 1a topically administered as a solution at 2% or 6% reduced ear swelling highly significantly by 72 or 86%, respectively.

One of the most undesirable side-effects of corticosteroid administration is immunosuppression, which leads to the inability to effectively address parasitic infection, wound healing and tumor growth. In the current study, the local lymph node reaction after TDI challenge (lymph node weight and cell number) was determined to assess the response of immune organs. Systemic treatment with compound 1a at 100 mg/kg or topical treatment at 2% or 6% did not have any impact on the local lymph node reaction.

In view of the strong effect shown in the allergic contact dermatitis model, the compounds of the present invention and, including compound 1a, are particularly effective and thus useful for the topical pharmaceutical intervention in inflammatory diseases, in particular in atopic dermatitis.

The invention claimed is:
1. A compound of the following formula 1

$$R^5-R^4-X\genfrac{}{}{0pt}{}{R^3}{\genfrac{}{}{0pt}{}{|}{\underset{R^1}{\overset{}{\diagdown}R^2}}}$$

1 or a pharmaceutically acceptable salt, solvate, or prodrug thereof, wherein:

$R^1$ is a $C_{10-20}$ hydrocarbon group;

$R^2$ is a $C_{1-4}$ alkyl group, and $R^3$ is H;

$R^4$ is a $C_{1-6}$ hydrocarbon group;

$R^5$ is $-SO_3$, $-SO_3H$, $-PO_3^{2-}$, $-PO_3H_2$, $-PO_2(OC_{1-3}$ alkyl), $-PO_2H(OC_{1-3}$alkyl), $-PO(OC_{1-3}$ alkyl$)_2$, $-CO_2$, $-CO_2H$ or $-CO_2(C_{1-3}$ alkyl; and X is $N^+$.

2. The compound of claim 1, wherein $R^5$ is $-SO_3$ or $-SO_3H$.

3. The compound of claim 1, wherein $R^5$ is $-PO_3^{2-"}$, $-PO_3H^-$, or $-PO_3H_2$.

4. The compound of claim 1, wherein $R^4$ is $-(CH_2)_3-$.

5. The compound of claim 1, wherein $R^1$ is a linear $C_{10-20}$ alkyl group, a linker $C_{10-20}$ alkenyl group, or a linear $C_{10-20}$ alkynyl group.

6. The compound of claim 1, wherein $R^1$ is $-(CH_2)_{11}-CH_3$, $-(CH_2)_{13}-CH_3$, or $-(CH_2)_{15}-CH_3$.

7. The compound of claim 1, wherein $R^2$ is methyl.

8. The compound of claim 1, wherein the compound is a compound of any of the following formulae:

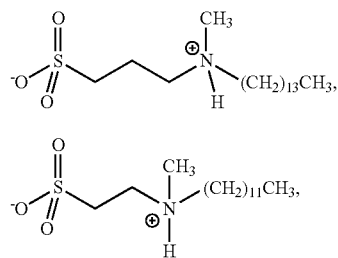

1b

1q

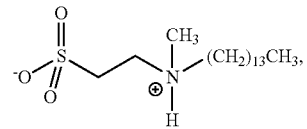

1s

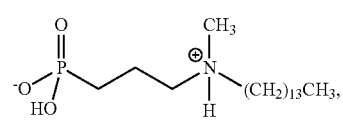

1u

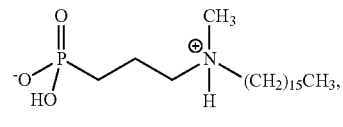

1v

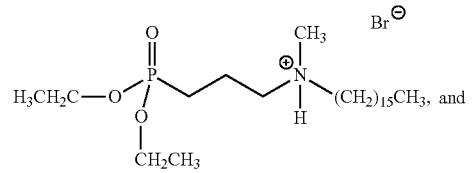

1w

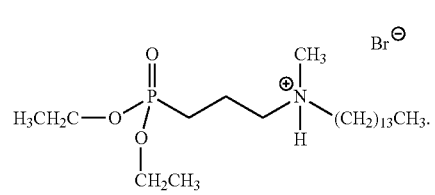

1x

9. A pharmaceutical composition comprising the compound of claim 1 and a pharmaceutically acceptable excipient.

* * * * *